(12) United States Patent
Saulnier Sholler et al.

(10) Patent No.: US 8,470,815 B2
(45) Date of Patent: Jun. 25, 2013

(54) NITROFURAN COMPOUNDS FOR THE TREATMENT OF CANCER AND ANGIOGENESIS

(75) Inventors: Giselle L. Saulnier Sholler, Charlotte, VT (US); Narasimha Swamy, Warwick, RI (US); Hena Swamy, legal representative, Warwick, RI (US); Satyan Kalkunte, Barrington, RI (US); Rakesh K. Singh, Barrington, RI (US); Laurent Brard, Cranston, RI (US); Kyu Kwang Kim, Cranston, RI (US)

(73) Assignees: Brown University, Providence, RI (US); Women and Infants' Hospital Rhode Island, Providence, RI (US)

( * ) Notice: Subject to any disclaimer, the term of this patent is extended or adjusted under 35 U.S.C. 154(b) by 640 days.

(21) Appl. No.: 12/225,202

(22) PCT Filed: Mar. 7, 2007
(Under 37 CFR 1.47)

(86) PCT No.: PCT/US2007/005927
§ 371 (c)(1),
(2), (4) Date: Jun. 7, 2011

(87) PCT Pub. No.: WO2007/108947
PCT Pub. Date: Sep. 27, 2007

(65) Prior Publication Data
US 2011/0288080 A1  Nov. 24, 2011

Related U.S. Application Data

(60) Provisional application No. 60/782,756, filed on Mar. 16, 2006.

(51) Int. Cl.
*A61K 31/54* (2006.01)

(52) U.S. Cl.
USPC .................................................. 514/227.8

(58) Field of Classification Search
USPC .................................................. 514/227.8
See application file for complete search history.

(56) References Cited

U.S. PATENT DOCUMENTS
2005/0169935 A1    8/2005  Aylsworth et al.

FOREIGN PATENT DOCUMENTS
| EP | 1 537 858 A1 | 6/2005 |
| GB | 2021111 A | 11/1979 |
| WO | WO 2008/091946 A2 | 7/2008 |

OTHER PUBLICATIONS

Karol, Nitrofurans in treatment of malignant testicular tumors. J Urol. Jul. 1960;84:120-2.
Sur et al., Studies on the antineoplasticity of Schiff bases containing 5-nitrofuran and pyrimidine. Oncology. 1990;47(5):433-8.

*Primary Examiner* — Brandon Fetterolf
*Assistant Examiner* — Christopher R Stone
(74) *Attorney, Agent, or Firm* — Boulware & Valoir

(57) ABSTRACT

The invention is directed to the synthesis and use of nitrofuran compounds, especially Nifurtimox, as medicaments to treat cancer, especially neuroblastoma, and to inhibit angiogenesis. The invention also provides compositions, unit dosage forms, and kits comprising the compounds.

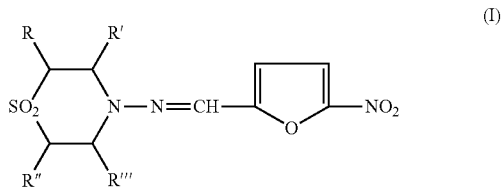

12 Claims, 13 Drawing Sheets

VEHICLE − GROWTH FACTOR

VEHICLE + GROWTH FACTOR

GF + NIFURTIMOX 20 µg/ml

NITROFURAN COMPOUNDS FOR THE TREATMENT OF CANCER AND ANGIOGENESIS

CROSS REFERENCE TO RELATED APPLICATIONS

This application is a national stage filing under 35 U.S.C. §371 of PCT International application PCT/US2007/005927 designating the United States of America, filed Mar. 7, 2007, which claims the benefit under 35 U.S.C. §119(e) of U.S. provisional application serial number 60/782,756, filed Mar. 16, 2006, both of which are incorporated herein by reference.

FIELD OF THE INVENTION

The invention relates to the synthesis and use of nitrofuran compounds (for example, Nifurtimox) to treat cancer and inhibit angiogenesis. The invention also provides therapeutic compositions and kits comprising nitrofuran compounds.

BACKGROUND

Cancer is the second leading cause of death in the United States. Due to the ever increasing aging population in the United States, it is reasonable to expect that rates of cancer incidence will continue to grow. Cancer is currently treated using a variety of modalities including surgery, radiation therapy and chemotherapy. The choice of treatments depends upon the type, location and dissemination of the cancer. One of the advantages of surgery and radiation therapy is the ability to control to some extent the impact of the therapy, and thus to limit the toxicity to normal tissues in the body. Chemotherapy is arguably the most appropriate treatment for disseminated cancers such as leukemia and lymphoma as well as metastases. Chemotherapy is generally administered systemically and thus toxicity to normal tissues is a major concern. Not all tumors, however, respond to chemotherapeutic agents and others, although initially responsive to chemotherapeutic agents, may develop resistance. Thus there is a need for a better understanding of the mechanisms underlying the formation and progression of cancer and the development of resistance to treatment. There is also a need for more effective cancer treatments.

Evidence has accumulated over the past several years to support the hypothesis that angiogenesis promotes the growth and progression of solid tumors and leukemias. Angiogenesis favors the transition from hyperplasia to neoplasia i.e. the passage from a state of cellular multiplication to a state of uncontrolled proliferation characteristic of tumor cells. Angiogenesis also influences the dissemination of cancer cells throughout the entire body eventually leading to metastasis formation.

More recent evidence implicates angiogenesis in the pathogenesis of diseases other than cancer. For example, angiogenesis seems to provide a conduit for the entry of inflammatory cells into sites of chronic inflammation (e.g., Crohn's disease and chronic cystitis) and destroys cartilage in rheumatoid arthritis. Angiogenesis also contributes to growth and hemorrhage of atherosclerotic plaques, leads to intraperitoneal bleeding in endometriosis, and is a cause of blindness. Angiogenesis has also been implicated in the pathogenesis of other diseases and as a result the search for effective angiogenesis inhibitors has intensified. Several angiogenesis inhibitors have recently been discovered and some are currently in clinical trials.

Neuroblastoma is a leading cause of cancer death in children; it is the most common extracranial solid tumor in children, and it carries a poor prognosis. Current treatments of intensive chemotherapy, surgery, radiation and autologous bone marrow transplant are often unsuccessful leaving the patients uncured, weak, and unable to tolerate more intense treatment. Currently most children greater than 1 year of age fail standard therapies. Only 30% of these children survive up to 5 years after diagnosis[1,2]. New advancements in treatment strategies are therefore needed to improve the overall survival rate in neuroblastoma.

SUMMARY OF THE INVENTION

The invention provides methods for the improved synthesis of nitrofuran compounds, as well as methods and compositions for the treatment of cancers and for inhibiting angiogenesis in mammalian, especially human, subjects. The invention is based in part on the serendipitous discovery that Nifurtimox, a known nitrofuran compound used as an anti-fungal agent, reduced the size of a neuroblastoma tumor in a patient who was being treated with Nifurtimox for Chagas disease. Nifurtimox was also found to inhibit proliferation of neuroblastoma cells in vitro. The invention is also based in part on the discovery that Nifurtimox inhibits angiogenesis.

Nifurtimox belongs to a group of compounds known as nitrofurans (FIG. 1). Nitrofurans (including Nifurtimox) are nitroheterocyclic compounds, may of which have biological activity against protozoan and bacterial infections in mammals.[4] To date, the nitrofurans have not been investigated for use in the treatment of human cancers because of observed toxic effects in veterinary animals. For example, nitrofurazone, a veterinary antimicrobial, was found to cause mammary and ovarian tumors in animals.[5]

The novel observation that Nifurtimox reduces tumor size, inhibits proliferation of neuroblastoma cells, and inhibits angiogenesis indicates that Nifurtimox and other nitrofuran compounds can be used to treat cancer and diseases or disorders that are mediated or caused by angiogenesis. Some of these diseases and disorders are recited herein as targets of the therapy.

Thus, in one aspect the invention provides a method for treating a mammalian, preferably a human, subject having a cancer. The method comprises administering to that subject a nitrofuran compound in an effective amount to treat the cancer. The cancer may be a metastatic cancer. In preferred embodiments, it may be a solid tumor, for example a neuroblastoma, medulloblastoma, peripheral malignant nerve sheath tumor, ependymoma, craniopharyngioma, astrocytoma (juvenile pilocytic astrocytoma, subependymal giant cell astrocytoma, pleimorphic xanthoastrocytoma, anaplastic astrocytoma, or gliomatosis cerebri), meningioma, germinoma, glioma, mixed glioma, choroid plexus tumor, oligodendroglioma (mixed glioma (e.g., oligoastrocytoma) or anaplastic oligodendroglioma), peripheral neuroectodermal tumor, primitive neuroectodermal tumor (PNET), CNS lymphoma, pituitary adenoma, or Schwannoma. In some especially preferred embodiments, the cancer is a neuroblastoma or medulloblastoma. In any embodiment, the subject may be free of other indication calling for treatment with the nitrofuran, i.e., it is not required that the subject also have Chagas disease or some other condition caused by a microbial infection for example. The method may additionally comprise treating the subject with chemotherapy, surgery and/or radiation therapy.

In another aspect, the invention provides a method for inhibiting angiogenesis in a mammalian, preferably a human, subject. The method comprises administering to that subject a nitrofuran compound in an effective amount to inhibit angiogenesis. The subject may have a cancer, an ocular disease (for example, macular degeneration, a maculopathy, diabetic retinopathy, or retinopathy of prematurity (retrolental fibroplasia)), a skin disease (for example, infantile hemangioma, verruca vulgaris, psoriasis, neurofibromatosis, or epidermolysis bullosa), an autoimmune disease (for example, rheumatoid arthritis), a gynecologic disease (for example, endometrial polyp, endometriosis, dysfunctional uterine bleeding, ovarian hyperstimulation syndrome, polycystic ovary syndrome (PCO), or preeclempsia), a cardiovascular disease (for example, coronary artery disease, ischemic cardiomyopathy, myocardial ischemia, arteriosclerosis, atherosclerosis, atherosclerotic plaque neovascularization, arterial occlusive disease, ischemia, ischemic ulcers, ischemic or post-myocardial ischemia revascularization, peripheral vascular diseases, or intermittent claudication), or a gastrointestinal disease (for example, Crohn's disease and ulcerative colitis, Buerger Disease, thromboangiitis obliterans, arteriosclerosis obliterans, ischemic ulcers, multiple sclerosis, idiopathic pulmonary fibrosis, HIV infection, plantar fasciitis, Von Hippel-Landau Disease, CNS hemangioblastoma, retinal hemangioblastoma, thyroiditis, benign prostatic hypertrophy, glomerulonephritis, ectopic bone formation, or keloids). The cancer may be biliary tract cancer; bladder cancer; bone cancer; brain or CNS cancer; breast cancer; cervical cancer; choriocarcinoma; colon and rectum cancer; connective tissue cancer; cancer of the digestive system; endometrial cancer; esophageal cancer; eye cancer; fibromael; cancer of the head and neck; gastric cancer; intra-epithelial neoplasm; kidney cancer; larynx cancer; leukemia including acute myeloid leukemia, acute lymphoid leukemia, chronic myeloid leukemia, chronic lymphoid leukemia; liver cancer; lung cancer (e.g. small cell and non-small cell); lymphoma including Hodgkin's and Non-Hodgkin's lymphoma; melanoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, a sarcoma, or a carcinoma. The cancer may be a metastatic cancer. In any embodiment, the subject may be otherwise free of any indication calling for treatment with the nitrofuran, for example free of Chagas disease. The method may additionally comprise treating the patient with chemotherapy, surgery and/or radiation therapy.

In another aspect, the invention provides pharmaceutical compositions for the treatment of the foregoing diseases, disorders, or conditions. The compositions comprise one or more than one nitrofuran compound in admixture with a pharmaceutically acceptable carrier. Preferably, the nitrofuran compound is Nifurtimox, Furazolidine or Nifuratel. More preferably, the nitrofuran compound is Nifurtimox. In one very specific aspect, the composition comprises a pharmaceutical unit dosage form comprising an amount of a nitrofuran compound, preferably Niturtimox, effective to treat a neuroblastoma or other related cancer, i.e., a central nervous system cancer. Preferably the unit dosage is about 200-300 mg of medicament, in admixture with a pharmaceutically acceptable carrier. In another very specific aspect, the compositions comprise a nitrofuran compound, especially Nifurtimox, and may also include ascorbic acid or buthionine sulfoximine as a second active ingredient or agent. These compositions may be formulated for oral, intrathecal, intravenous, or intramuscular administration; oral administration formulations are preferred.

In yet another aspect, the invention is a kit comprising a nitrofuran compound, for example Nifurtimox, in admixture with a suitable pharmaceutically acceptable carrier, formulated for oral, intrathecal, intravenous, or intramuscular administration. Oral formulation is preferable. The kit may also include ascorbic acid or buthionine sulfoximine or both in effective amount(s), likewise in suitable pharmaceutically acceptable carrier(s). The kit may further comprise instructions for use. In some embodiments the instructions for use instruct the health care provider how to administer Nifurtimox.

As noted above, the compositions, their uses and the kits may additionally include a second agent or ingredient. The second agent may be a glutathione antagonist or depletor. Examples of glutathione antagonists or depletors include but are not limited to buthionine sulfoximine, isothiocyanates, cyclophosphamide, ifosphamide, actinomycin D, or N-(4-hydroxyphenyl)retinamide (4-HPR). The second agent may be a pro-oxidant. Examples of pro-oxidants include but are not limited to ascorbic acid, hydrogen peroxide, and hydroquinone. Pro-oxidants are known to those of ordinary skill in the art. In some important embodiments the pro-oxidant (e.g., ascorbic acid) is administered simultaneously with or before the nitrofuran compound. The second agent may be a chemotherapeutic agent. Examples of some important chemotherapeutic agents include but not limited to topotecan, organometallics like cisplatin, paraplatin, doxorubicin, vincristine, vinblastine, taxol and congeners there from, actinomycin D. Exampls of these chemotherapeutic agents are listed below. The second agent may be a vascular disrupting agent. Examples of vascular disrupting agents include but are not limited to combretostatins, isothiocyanates both naturally occurring or synthetic derivatives and analogs thereof. The second agent may be an angiogenesis inhibitor. Examples of angiogenesis inhibitors include but are not limited to 2-methoxyestradiol (2-ME), AG3340, Angiostatin, Antithrombin III, Anti-VEGF antibody, Batimastat, bevacizumab (avastatin), BMS-275291, CAI, Canstatin, Captopril, Cartilage Derived Inhibitor (CDI), CC-5013, Celecoxib (CELEBREX®), COL-3, Combretastatin, Combretastatin A4 Phosphate, Dalteparin (FRAGIN®), EMD 121974 (Cilengitide), Endostatin, Erlotinib (TARCEVA®), gefitinib (Iressa), Genistein, Halofuginone Hydrobromide (TEMPOSTATINT™), Id1, Id3, IM862, imatinib mesylate, Inducible protein 10, Interferon-alpha, Interleukin 12, Lavendustin A, LY317615 or AE-941 (NEOVASTATT™), Marimastat, Maspin, Medroxpregesterone Acetate, Meth-1, Meth-2, Neovastat, Osteopontin cleaved product, PEX, Pigment epithelium growth factor (PEGF), Platelet factor 4, Prolactin fragment, Proliferin-related protein (PRP), PTK787/ZK 222584, Recombinant human platelet factor 4 (rPF4), Restin, Squalamine, SU5416, SU6668, Suramin, Taxol, Tecogalan, Thalidomide, Thrombospondin, TNP-470, Troponin I, Vasostatin, VEG1, VEGF-Trap, and ZD6474.

The angiogenesis inhibitor may be a VEGF antagonist. In some embodiments the VEGF antagonist is a VEGF binding molecule. The VEGF binding molecule may be a VEGF antibody or antigen binding fragment thereof. In some embodiments the VEGF antagonist is NeXstar.

The therapeutic composition of the invention may be administered orally, sublingually, buccally, intranasally, intravenously, intramuscularly, intrathecally, intracranially, intraperitoneally, subcutaneously, intradermally, topically, rectally, vaginally, intrasynovially or intravitreously.

In another aspect, the invention includes an improved method of making the nitrofuran compound and nitrofuran analogs of the invention. This method results in a more efficient and less hazardous synthesis of the side chain of nitrofuran and of nitrofuran analogs and is described in detail in the Detailed Description.

These and other aspects of the invention, as well as various advantages and utilities will be apparent with reference to the Detailed Description. Each aspect of the inventions can encompass various embodiments as will be understood.

DETAILED DESCRIPTION OF THE INVENTION

Figure 1:
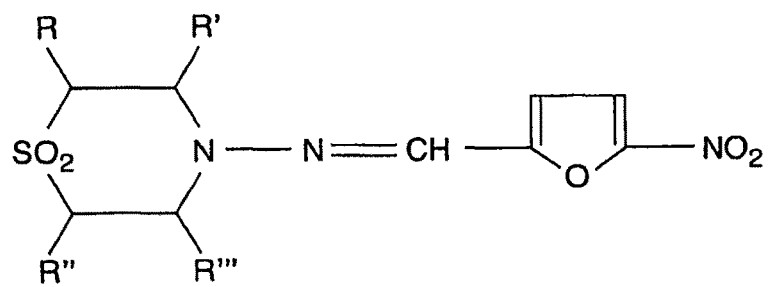
FIG. 1 is the structure of the backbone of a nitrofuran compound.

The invention is based, in part, on the serendipitous discovery (as detailed in Example 13) that the administration of 4-[5-Nitrofurfurylidene)amino]-3-methylthiomorpholine 1,1-dioxide, which is also referred to by it nonproprietary name "Nifurtimox", reduces tumor size, inhibits proliferation of neuroblastoma cells, and inhibits angiogenesis. Thus, the invention includes, in some aspects, administering to a subject having a cancer a nitrofuran compound in the form of a medicament to treat the cancer in the subject. The invention also includes, in some aspects, administering a nitrofuran compound to a subject to inhibit angiogenesis in the subject. The nitrofuran compound is administered in an effective and physiologically acceptable amount to treat the cancer in the subject. Although not wishing to be bound to any particular theory, we believe that Nifurtimox exerts its cytotoxic effect specifically by generating free radicals. Nifurtimox is a nitroheterocyclic compound; its nitro group can be reduced to the nitro anion radical in cell-free systems by interacting with cytochrome P-450 reductase, xanthine oxidase, ascorbate, and catecholamines. Nitro anions can then reduce oxygen to the superoxide anion radical and hydrogen peroxide. In Chagas disease, the nitro anion free radicals and oxyradicals have been shown to be cytotoxic for the parasite *T. Cruzi*. The reduction of the nitro group not only generates anion radicals, but interaction with catecholamines[3] appears also to generate semiquinone free radicals that exacerbate damage to functionally important biomolecules, leading to apoptosis of neuroblastoma cell lines. Neuroblastoma cells are known to contain high levels of catecholamines, thereby potentially leading to relatively specific targeting of these cells. The reaction with catecholamines in neuroblastoma cell lines was confirmed by the reduction of cytotoxicity by pretreatment with AMPT, a tyrosine hydroxylase inhibitor that reduces the total amount of catecholamine stored in cells. In addition, the enhanced sensitivity of sympathetic neurons—but not parsaympathetic neurons or non-neuronalcells—to nifurtimox supports this conclusion.

The term "treatment" or "treating" includes amelioration, cure or maintenance (i.e., the prevention of relapse) of a disorder. Treatment after a disorder has started aims to reduce, ameliorate or altogether eliminate the disorder, and/or its associated symptoms, to prevent it from becoming worse, or to prevent the disorder from re-occurring once it has been initially eliminated (i.e., to prevent a relapse).

A subject means a mammalian species, including but not limited to a dog, cat, horse, cow, pig, sheep, goat, chicken, rodent, or primate. Subjects can be house pets (e.g., dogs, cats), agricultural stock animals (e.g., cows, horses, pigs, chickens, etc.), laboratory animals (e.g., mice, rats, rabbits, etc.), zoo animals (e.g., lions, giraffes, etc.), but are not so limited. Preferred subjects are human subjects. The human subject may be a pediatric, adult or a geriatric subject.

As used herein the terms "nitrofuran(s)" and "nitrofuran compound(s)" are employed interchangeably and encompass furans having a side chain containing one or more nitrogen atoms. As is well known in the art, furan is an unsaturated aromatic heterocyclic compound composed of four carbon atoms and one oxygen atom. See Ege, Organic Chemistry, 3d. Ed., D.C. Heath & Co., Lexington, Mass. (1994). Examples of nitrofurans include, without limitation, Nifurtimox, Furazolidine and Nifuratel. See Raether W, Hanel H. Nitroheterocyclic Drugs with Broad Spectrum Acitivity, Parasit Res 2003; 90:S19-S39; Albrecht et al., J. Med. Chem. 13(4): 736 (1970); Albrecht et al., Arzneimittel-Forschung (Drug Res.) 21(1): 127-31 (1971); Pozas et al., Bioorganic & Medicinal Chemistry Letters 15: 1417-21 (2005). "Compound" includes both the synthetically prepared and administered nitrofuran compound and nitrofuran compounds produced in vivo after administration of another compound.

"Cancer" as used herein refers to an uncontrolled growth of cells which interferes with the normal functioning of the bodily organs and systems. Cancer cells which migrate from their original location and seed vital organs can eventually lead to the death of the subject through the functional deterioration of the affected organs. A cancer cell is a cell that divides and reproduces abnormally due to a loss of normal growth control. Cancer cells almost always arise from at least one genetic mutation. In some instances, it is possible to distinguish cancer cells from their normal counterparts based on profiles of expressed genes and proteins, as well as to the level of their expression. Genes commonly affected in cancer cells include oncogenes, such as ras, neu/HER2/erbB, myb, myc and abl, as well as tumor suppressor genes such as p53, Rb, DCC, RET and WT. Cancer-related mutations in some of these genes lead to a decrease in their expression or a complete deletion. In others, mutations cause an increase in expression or the expression of an activated variant of the normal counterpart.

The term "tumor" is usually equated with neoplasm, which literally means "new growth" and is used interchangeably with "cancer." A "neoplastic disorder" is any disorder associated with cell proliferation, specifically with a neoplasm. A "neoplasm" is an abnormal mass of tissue that persists and proliferates after withdrawal of the carcinogenic factor that initiated its appearance. There are two types of neoplasms, benign and malignant. Nearly all benign tumors are encapsulated and are noninvasive; in contrast, malignant tumors are almost never encapsulated but invade adjacent tissue by infiltrative destructive growth. This infiltrative growth can be followed by tumor cells implanting at sites discontinuous with the original tumor.

A metastasis is a region of cancer cells, distinct from the primary tumor location resulting from the dissemination of cancer cells from the primary tumor to other parts of the body. At the time of diagnosis of the primary tumor mass, the subject may be monitored for the presence of metastases. Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

The method of the invention can be used to treat cancer in a subject. In some embodiments, the cancer is a central nervous system (CNS) cancer. Examples of some important CNS cancers include, but are not limited to, neuroblastoma, medulloblastoma, peripheral malignant nerve sheath tumor, ependymoma, chraniopharyngioma, astrocytoma, meningioma, germinoma, glioma, mixed glioma, choroid plexus tumor, oligodendroglioma, peripheral neuroectodermal tumor, primitive neuroectodermal tumor (PNET), CNS lymphoma, pituitary adenoma, and Schwannoma. In some embodiments the astrocytoma is Grade I, Grade II, Grade III, or Grade IV. The astrocytoma may be a low-grade or a high-grade. The astrocytoma may be juvenile pilocytic astrocytoma, subependymal giant cell astrocytoma, pleimorphic xanthoastrocytoma, anaplastic astrocytoma, or gliomatosis cerebri. In some embodiments the oligodendroglioma is a mixed glioma (oligoastrocytoma) or an anaplastic oligodendroglioma. In one preferred embodiment, the cancer is neuroblastoma.

Other cancers that can be treated by the methods of this invention include but are not limited to basal cell carcinoma, biliary tract cancer, bladder cancer, bone cancer, brain and CNS cancer, breast cancer, cervical cancer, choriocarcinoma, colon and rectum cancer, connective tissue cancer, cancer of the digestive system, endometrial cancer, esophageal cancer, eye cancer, fibroma, cancer of the head and neck, gastric cancer, intra-epithelial neoplasm, kidney cancer, larynx cancer, leukemia including acute myeloid leukemia, acute lymphoid leukemia, chronic myeloid leukemia, chronic lymphoid leukemia, liver cancer, lung cancer (e.g. small cell and non-small cell), lymphoma including Hodgkin's and Non-Hodgkin's lymphoma, melanoma, oral cavity cancer (e.g., lip, tongue, mouth, and pharynx), ovarian cancer, pancreatic cancer, prostate cancer, retinoblastoma, rhabdomyosarcoma, rectal cancer, renal cancer, cancer of the respiratory system, sarcoma, skin cancer, stomach cancer, testicular cancer, thyroid cancer, uterine cancer, cancer of the urinary system, as well as other carcinomas and sarcomas.

Carcinomas are cancers of epithelial origin. Carcinomas intended for treatment with the methods of the invention include, but are not limited to, acinar carcinoma, acinous carcinoma, alveolar adenocarcinoma (also called adenocystic carcinoma, adenomyoepithelioma, cribriform carcinoma and cylindroma), carcinoma adenomatosum, adenocarcinoma, carcinoma of adrenal cortex, alveolar carcinoma, alveolar cell carcinoma (also called bronchiolar carcinoma, alveolar cell tumor and pulmonary adenomatosis), basal cell carcinoma, carcinoma basocellulare (also called basaloma, or basiloma, and hair matrix carcinoma), basaloid carcinoma, basosquamous cell carcinoma, breast carcinoma, bronchioalveolar carcinoma, bronchiolar carcinoma, bronchogenic carcinoma, cerebriform carcinoma, cholangiocellular carcinoma (also called cholangioma and cholangiocarcinoma), chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epibulbar carcinoma, epidermoid carcinoma, carcinoma epitheliale adenoides, carcinoma exulcere, carcinoma fibrosum, gelatiniform carcinoma, gelatinous carcinoma, giant cell carcinoma, gigantocellulare, glandular carcinoma, granulosa cell carcinoma, hair-matrix carcinoma, hematoid carcinoma, hepatocellular carcinoma (also called hepatoma, malignant hepatoma and hepatocarcinoma), Hürthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, lenticular carcinoma, carcinoma lenticulare, lipomatous carcinoma, lymphoepithelial carcinoma, carcinoma mastitoides, carcinoma medullare, medullary carcinoma, carcinoma melanodes, melanotic carcinoma, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, carcinoma nigrum, oat cell carcinoma, carcinoma ossificans, osteoid carcinoma, ovarian carcinoma, papillary carcinoma, periportal carcinoma, preinvasive carcinoma, prostate carcinoma, renal cell carcinoma of kidney (also called adenocarcinoma of kidney and hypernephoroid carcinoma), reserve cell carcinoma, carcinoma sarcomatodes, scheinderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, carcinoma vilosum.

Sarcomas are rare mesenchymal neoplasms that arise in bone and soft tissues. Different types of sarcomas are recognized and these include: liposarcomas (including myxoid liposarcomas and pleiomorphic liposarcomas), leiomyosarcomas, rhabdomyosarcomas, malignant peripheral nerve sheath tumors (also called malignant schwannomas, neurofibrosarcomas, or neurogenic sarcomas), Ewing's tumors (including Ewing's sarcoma of bone, extraskeletal (i.e., non-bone) Ewing's sarcoma, and primitive neuroectodermal tumor [PNET]), synovial sarcoma, angiosarcomas, hemangiosarcomas, lymphangiosarcomas, Kaposi's sarcoma, hemangioendothelioma, fibrosarcoma, desmoid tumor (also called aggressive fibromatosis), dermatofibrosarcoma protuberans (DFSP), malignant fibrous histiocytoma (WIFE), hemangiopericytoma, malignant mesenchymoma, alveolar soft-part sarcoma, epithelioid sarcoma, clear cell sarcoma, desmoplastic small cell tumor, gastrointestinal stromal tumor (GIST) (also known as GI stromal sarcoma), osteosarcoma (also known as osteogenic sarcoma)-skeletal and extraskeletal, and chondrosarcoma.

The cancers to be treated may be refractory cancers. As used herein, a refractory cancer is a cancer that is resistant to the ordinary standard of care prescribed. These cancers may appear initially responsive to a treatment and then recur, or they may be completely non-responsive to the treatment. Subjects being treated according to the invention for a refractory cancer therefore may have already been exposed to another treatment for their cancer. Alternatively, if the cancer is likely to be refractory (e.g., given an analysis of the cancer cells or history of the subject), then the subject may not have already been exposed to another treatment. Examples of refractory cancers include but are not limited to leukemias, melanomas, renal cell carcinomas, colon cancer, liver (hepatic) cancers, pancreatic cancer, Non-Hodgkin's lymphoma, and lung cancer.

The invention can also be used to treat cancers that are immunogenic. Cancers that are immunogenic are cancers that are known to (or likely to) express immunogens on their surface or upon cell death. These immunogens are in vivo endogenous sources of cancer antigens and their release can be exploited by the methods of the invention in order to treat the cancer. Examples of immunogenic cancers include malignant melanoma and renal cell cancer. Mantel Cell Lymphoma, follicular lymphoma, diffuse large B-cell lymphoma, T-cell acute lymphoblastic leukemia, Burkitt lymphoma, myeloma, immunocytoma, acute promyelocytic leukemia, chronic myeloid/acute lymphoblastic leukemia, acute leukemia, B-cell acute lymphoblastic leukemia, anaplastic large cell leukemia, myelodysplastic syndrome/acute myeloid leukemia, Non-Hodgkin's lymphoma, chronic lymphocytic leukemia (CLL), acute lymphoblastic leukemia (ALL). acute myelogenous leukemia (AML), Common (pre-B) acute lymphocytic leukemia, malignant melanoma, T-cell lymphoma, leukemia, B-cell lymphoma, epithelial malignancies, lymphoid malignancies, gynecological carcinomas, biliary adenocarcinomas, and ductal adenocarcinomas of the pancreas.

The invention involves in some other aspects, methods for inhibiting angiogenesis in a subject. Angiogenesis is an abnormal rapid proliferation of endothelial cells resulting in persistent and unabated formation of abnormal new blood vessels (microvessels). Angiogenesis that continues for months or years can support the growth and progression of cancer and may result in damage to various organs and tissues such as, for example, the eye, skin, heart, blood vessels, lung, gastrointestinal tract, and the genitourinary tract. The methods of the invention involve administering to a subject a nitrofuran compound in an effective amount to inhibit the angiogenesis. The nitrofuran compound is administered in an effective amount to inhibit the angiogenesis in the subject. Preferably the compound is Niturtimox, and the subject is a human subject.

As used herein the term "inhibits angiogenesis" refers to the reduction of the number or density of the abnormal microvessels. A reduction of the number of abnormal microvessels refers to decreasing the number of existing abnormal microvessels or decreasing the production of new microvessels. Reduction, as used herein, includes total elimination or eradication, as well as other decreases which do not result in total eradication.

Angiogenesis may be assesed by various methods or techniques. The most widely used method in clinical settings relies on histochemical or immunohistochemical staining of blood vessels (microvessels) in biopsies (open or needle) or specimens. Features of angiogenesis that may be examined include, for example, blood vessel density and/or the morphology and/or thickness of the perivascular cuff. Areas of microvessel density in a histologic biopsy or specimen are quantified. Areas of high microvessel density ("hot spots") may, for example, contain the most tumor cells and/or have the highest chance of metastasizing. One technique of determining microvessel density is by measuring intercapillary distance. Another method of assessing angiogenesis is measuring perivascular cuff thickness. An increase in the thickness of the preivascular cuff is associated with progression of the angiogenesis and may be indicative of disease worsening.

Angiogenesis may also be assessed by measuring blood, serum, plasma, or tissue levels of angiogenesis (angiogenic) factors. Levels of angiogenic factors serve as a surrogate marker of angiogenesis. Examples of angiogenic factors that may serve as surrogate markers of angiogenesis include but are not limited to Angiogenin, Angiopoietin-1, Del-1, Fibroblast growth factors: acidic (aFGF) and basic (bFGF), Follistatin, Granulocyte colony-stimulating factor (G-CSF), Hepatocyte growth factor (HGF)/scatter factor (SF), Interleukin-8 (IL-8), Leptin, Midkine, Placental growth factor, Platelet-derived endothelial cell growth factor (PD-ECGF), Platelet-derived growth factor-BB (PDGF-BB), Pleiotrophin (PTN), Progranulin, Proliferin, Transforming growth factor-alpha (TGF-alpha), Transforming growth factor-beta (TGF-beta), Tumor necrosis factor-alpha (TNF-alpha), Vascular endothelial growth factor (VEGF)/vascular permeability factor (VPF). Imaging techniques are also useful for the assesment of angiogenesis. Suitable imaging techniques or devices include non-invasive devices such as CT, rotational CT, micro-CT, multiple energy computed tomography (MECT), single detector CT (SDCT), multi-detector CT (MDCT), volumetric CT (VCT), MRI, micro-MR, X-ray, rotational X-ray, PET, near infrared/optical and other non-invasive scanning techniques and devices that may be used outside a subject's body or inserted non-invasively into a body cavity. Angiogenesis may also be imaged by CT angiography (CTA), tomosynthesis, X-ray micro-angiography, and by other techniques. One angiogenesis imaging technique involves the use microbubble-based contrast agents (SonoVue) combined with ultrasound and contrast specific imaging modalities to detect perfusion changes on tumor microvascular perfusion. Other angiogenesis imaging techniques include color Doppler and mammography. Color Doppler imaging can demonstrate angiogenesis in tumors such as breast cancer. Mammography may reveal the vascularized rim of a breast tumor. A wide range of imaging or radiologic signs may be enhanced by dyes.

Angiogenesis may also be assessed in a subject by a process that involves introducing at least one contrast agent into a body region of interest. For example, a contrast agent for detecting blood vessels may be injected into a blood vessel. A small amount of contrast agent may be introduced locally to enhance the detection of blood vessels in a particular body region of interest. Alternatively, a contrast agent may be provided in an amount sufficient to enhance the detection of blood vessels in a large body region or in the entire subject body. Structure data may be obtained for the body of the subject, or may be obtained for one or more target organs e.g., a lung, heart, breast, colon, etc., portion of an organ, or another target volume of the subject's body. A target volume can be any portion of the subject's body. e.g., a limb, the abdomen, the torso, the neck, the head, or any portion thereof. Other methods or techniques to assess angiogenesis not described herein may be used for the purpose of this invention. Methods and techniques to assess angiogenesis are known to those of ordinary skill in the art.

The nitrofurans may be administered in combination with other therapies, such as for example radiation therapy, surgery, conventional chemotherapy or with a combination of one or more additional therapies.

The nitrofurans may be administered alone in a pharmaceutical composition, or combined with therapeutically effective and physiologically acceptable amounts of one or more other active ingredients or agents. Such other active ingredients include, but are not limited to, glutathione antagonists, angiogenesis inhibitors, chemotherapeutic agent(s), and antibodies (e.g., cancer antibodies). The nitrofuran compound and the other active ingredients or agents may be administered simultaneously or sequentially. When the nitrofuran compound is administered simultaneously with another active agent or combined with another active ingredient, the nitrofuran compound and the other active ingredient may be administered in the same or separate formulations, but are administered at the same time. The other active agents may be administered sequentially with one another and with the nitrofuran compound when the administration of the other active agent and the nitrofuran is temporally separated. The separation in time between administrations may be a matter of minutes, hour, days, or it may be longer.

Examples of glutathione antagonists include but are not limited to buthionine sulfoximine, cyclophosphamide, ifosphamide, actinomycin D, and N-(4-hydroxyphenyl) retinamide (4-HPR).

Examples of angiogenesis inhibitors include but are not limited to 2-methoxyestradiol (2-ME), AG3340, Angiostatin, Antithrombin III, Anti-VEGF antibody, Batimastat, bevacizumab (avastatin), BMS-275291, CAI, Canstatin, Captopril, Cartilage Derived Inhibitor (CDI), CC-5013, Celecoxib (CELEBREX®), COL-3, Combretastatin, Combretastatin A4 Phosphate, Dalteparin (FRAGIN®), EMD 121974 (Cilengitide), Endostatin, Erlotinib (TARCEVA®), gefitinib (Iressa), Genistein, Halofuginone Hydrobromide (TEMPOSTATINT™), Id1, Id3, IM862, imatinib mesylate, Inducible protein 10, Interferon-alpha, Interleukin 12, Lavendustin A, LY317615 or AE-941 (NEOVASTATT™), Marimastat, Maspin, Medroxpregesterone Acetate, Meth-1, Meth-2, Neovastat, Osteopontin cleaved product, PEX, Pigment epithelium growth factor (PEGF), Platelet factor 4, Prolactin fragment, Proliferin-related protein (PRP), PTK787/ZK 222584, Recombinant human platelet factor 4 (rPF4), Restin, Squalamine, SU5416, SU6668, Suramin, Taxol, Tecogalan, Thalidomide, Thrombospondin, TNP-470, Troponin I, Vasostatin, VEG1, VEGF-Trap, and ZD6474. In some embodiments the angiogenesis inhibitor is a VEGF antagonist. The VEGF antagonist may be a VEGF binding molecule. VEGF binding molecules includeVEGF antibodies or antigen binding fragment(s) thereof. One example of a VEGF antagonist is NeXstar.

Examples of categories of chemotherapeutic agents that may be used as an additional active ingredient include but are not limited to DNA damaging agents and these include topoisomerase inhibitors (e.g., etoposide, ramptothecin, topotecan, teniposide, mitoxantrone), anti-microtubule agents (e.g., vincristine; vinblastine), anti-metabolic agents (e.g., cytarabine, methotrexate, hydroxyurea, 5-fluorouracil, floxuridine, 6-thioguanine, 6-mercaptopurine, fludarabine, pentostatin, chlorodeoxyadenosine), DNA alkylating agents (e.g., cisplatin, mechlorethamine, cyclophosphamide, ifosfamide, melphalan, chorambucil, busulfan, thiotepa, carmustine, lomustine, carboplatin, dacarbazine, procarbazine), and DNA strand break inducing agents (e.g., bleomycin, doxorubicin, daunorubicin, idarubicin, mitomycin C). Chemotherapeutic agents include synthetic, semisynethetic and naturally derived agents. Important chemotherapeutic agents include but are not limited to Acivicin, Aclarubicin, Acodazole Hydrochloride, Acronine, Adozelesin, Adriamycin, Aldesleukin, Alitretinoin, Allopurinol Sodium, Altretamine, Ambomycin, Ametantrone Acetate, Aminoglutethimide, Amsacrine, Anastrozole, Annonaceous Acetogenins, Anthramycin, Asimicin, Asparaginase, Asperlin, Azacitidine, Azetepa, Azotomycin, Batimastat, Benzodepa, Bexarotene, Bicalutamide, Bisantrene Hydrochloride, Bisnafide Dimesylate, Bizelesin, Bleomycin Sulfate, Brequinar Sodium, Bropirimine, Bullatacin, Busulfan, Cabergoline, Cactinomycin, Calusterone, Caracemide, Carbetimer, Carboplatin, Carmustine, Carubicin Hydrochloride, Carzelesin, Cedefingol, Celecoxib, Chlorambucil, Cirolemycin, Cisplatin, Cladribine, Crisnatol Mesylate, Cyclophosphamide, Cytarabine, Dacarbazine, DACA (N-[2-Dimethyl-amino)ethyl]acridine-4-carboxamide), Dactinomycin, Daunorubicin Hydrochloride, Daunomycin, Decitabine, Denileukin Diftitox, Dexormaplatin, Dezaguanine, Dezaguanine Mesylate, Diaziquone, Docetaxel, Doxorubicin, Doxorubicin Hydrochloride, Droloxifene, Droloxifene Citrate, Dromostanolone Propionate, Duazomycin, Edatrexate, Eflornithine Hydrochloride, Elsamitrucin, Enloplatin, Enpromate, Epipropidine, Epirubicin Hydrochloride, Erbulozole, Esorubicin Hydrochloride, Estramustine, Estramustine Phosphate Sodium, Etanidazole, Ethiodized Oil 1131, Etoposide, Etoposide Phosphate, Etoprine, Fadrozole Hydrochloride, Fazarabine, Fenretinide, Floxuridine, Fludarabine Phosphate, Fluorouracil, 5-FdUMP, Fluorocitabine, Fosquidone, Fostriecin Sodium, FK-317, FK-973, FR-66979, FR-900482, Gemcitabine, Gemcitabine Hydrochloride, Gemtuzumab Ozogamicin, Gold Au 198, Goserelin Acetate, Guanacone, Hydroxyurea, Idarubicin Hydrochloride, Ifosfamide, Ilmofosine, Interferon Alfa-2a, Interferon Alfa-2b, Interferon Alfa-n1, Interferon Alfa-n3, Interferon Beta-I a, Interferon Gamma-I b, Iproplatin, Irinotecan Hydrochloride, Lanreotide Acetate, Letrozole, Leuprolide Acetate, Liarozole Hydrochloride, Lometrexol Sodium, Lomustine, Losoxantrone Hydrochloride, Masoprocol, Maytansine, Mechlorethamine Hydrochloride, Megestrol Acetate, Melengestrol Acetate, Melphalan, Menogaril, Mercaptopurine, Methotrexate, Methotrexate Sodium, Methoxsalen, Metoprine, Meturedepa, Mitindomide, Mitocarcin, Mitocromin, Mitogillin, Mitomalcin, Mitomycin, Mytomycin C, Mitosper, Mitotane, Mitoxantrone Hydrochloride, Mycophenolic Acid, Nocodazole, Nogalamycin, Oprelvekin, Ormaplatin, Oxisuran, Paclitaxel, Pamidronate Disodium, Pegaspargase, Peliomycin, Pentamustine, Peplomycin Sulfate, Perfosfamide, Pipobroman, Piposulfan, Piroxantrone Hydrochloride, Plicamycin, Plomestane, Porfimer Sodium, Porfiromycin, Prednimustine, Procarbazine Hydrochloride, Puromycin, Puromycin Hydrochloride, Pyrazofurin, Riboprine, Rituximab, Rogletimide, Rolliniastatin, Safingol, Safingol Hydrochloride, Samarium/Lexidronam, Semustine, Simtrazene, Sparfosate Sodium, Sparsomycin, Spirogermanium Hydrochloride, Spiromustine, Spiroplatin, Squamocin, Squamotacin, Streptonigrin, Streptozocin, Strontium Chloride Sr 89, Sulofenur, Talisomycin, Taxane, Taxoid, Tecogalan Sodium, Tegafur, Teloxantrone Hydrochloride, Temoporfin, Teniposide, Teroxirone, Testolactone, Thiamiprine, Thioguanine, Thiotepa, Thymitaq, Tiazofurin, Tirapazamine, Tomudex, TOP-53, Topotecan Hydrochloride, Toremifene Citrate, Trastuzumab, Trestolone Acetate, Triciribine Phosphate, Trimetrexate, Trimetrexate Glucuronate, Triptorelin, Tubulozole Hydrochloride, Uracil Mustard, Uredepa, Valrubicin, Vapreotide, Verteporfin, Vinblastine, Vinblastine Sulfate, Vincristine, Vincristine Sulfate, Vindesine, Vindesine Sulfate, Vinepidine Sulfate, Vinglycinate Sulfate, Vinleurosine Sulfate, Vinorelbine Tartrate, Vinrosidine Sulfate, Vinzolidine Sulfate, Vorozole, Zeniplatin, Zinostatin, Zorubicin Hydrochloride, 2-Chlorodeoxyadenosine, 2'-Deoxyformycin, 9-aminocamptothecin, raltitrexed, N-propargyl-5,8-dideazafolic acid, 2-chloro-2'-arabino-fluoro-2'-deoxyadenosine, 2-chloro-2'-deoxyadenosine, anisomycin, trichostatin A, hPRL-G129R, CEP-751, linomide, sulfur mustard, nitrogen mustard (mechlor ethamine), cyclophosphamide, melphalan, chlorambucil, ifosfamide, busulfan, N-methyl-N-nitrosourea (MNU), N,N'-Bis(2-chloroethyl)-N-nitrosourea (BCNU), N-(2-chloroethyl)-N'-cyclohexyl-N-nitrosourea (CCNU), N-(2-chloroethyl)-N'-(trans-4-methylcyclohexyl-N-nitrosourea (MeCCNU), N-(2-chloroethyl)-N'-(diethyl)ethylphosphonate-N-nitrosourea (fotemustine), streptozotocin, diacarbazine (DTIC), mitozolomide, temozolomide, thiotepa, mitomycin C, AZQ, adozelesin, Cisplatin, Carboplatin, Ormaplatin, Oxaliplatin, CI-973, DWA 2114R, JM21.6, JM335, Bis (platinum), tomudex, azacitidine, cytarabine, gemcitabine, 6-Mercaptopurine, 6-Thioguanine, Hypoxanthine, teniposide, 9-amino camptothecin, Topotecan, CPT-11, Doxorubicin, Daunomycin, Epirubicin, darubicin, mitoxantrone, losoxantrone, Dactinomycin (Actinomycin D), amsacrine, pyrazoloacridine, all-trans retinol, 14-hydroxy-retro-retinol, all-trans retinoic acid, N-(4-Hydroxyphenyl)retinamide, 13-cis retinoic acid, 3-Methyl TTNEB, 9-cis retinoic acid, fludarabine (2-F-ara-AMP), and 2-chlorodeoxyadenosine (2-Cda).

Other chemotherapeutic agents include: 20-epi-1,25 dihydroxyvitamin D3, 5-ethynyluracil, abiraterone, aclarubicin, acylfulvene, adecypenol, adozelesin, aldesleukin, ALL-TK antagonists, altretamine, ambamustine, amidox, amifostine, aminolevulinic acid, amrubicin, amsacrine, anagrelide, anastrozole, andrographolide, angiogenesis inhibitors, antagonist D, antagonist G, antarelix, anti-dorsalizing morphogenetic protein-1, antiandrogen, prostatic carcinoma, antiestrogen, antineoplaston, antisense oligonucleotides, aphidicolin glycinate, apoptosis gene modulators, apoptosis regulators, apurinic acid, ara-CDP-DL-PTBA, arginine deaminase, asulacrine, atamestane, atrimustine, axinastatin 1, axinastatin 2, axinastatin 3, azasetron, azatoxin, azatyrosine, baccatin III derivatives, balanol, batimastat, BCR/ABL antagonists, benzochlorins, benzoylstaurosporine, beta lactam derivatives, beta-alethine, betaclamycin B, betulinic acid, bFGF inhibitor, bicalutamide, bisantrene, bisaziridinylspermine, bisnafide, bistratene A, bizelesin, breflate, bleomycin $A_2$, bleomycin $B_2$, bropirimine, budotitane, buthionine sulfoximine, calcipotriol, calphostin C, camptothecin derivatives (e.g., 10-hydroxy-catnptothecin), canarypox IL-2; capecitabine, carboxamide-amino-triazole, carboxyamidotriazole, CaRest M3, CARN 700, cartilage derived inhibitor, carzelesin, casein kinase inhibitors (ICOS), castanospermine, cecropin B, cetrorelix, chlorins, chloroquinoxaline sulfonamide, cicaprost, cis-porphyrin, cladribine, clomifene analogues, clotrimazole, collismycin A, collismycin B, combretastatin A4, combretastatin analogue, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, 2' deoxycoformycin (DCF), deslorelin, dexifosfamide, dexrazoxane, dexverapamil, diaziquone, didemnin B, didox, diethylnorspermine, dihydro-5-azacytidine, dihydrotaxol, dioxamycin, diphenyl spiromustine, discodermolide, docosanol, dolasetron, doxifluridine, droloxifene, dronabinol, duocarmycin SA, ebselen, ecomustine, edelfosine, edrecolomab, eflornithine, elemene, emitefur, epirubicin, epothilones (A, R=H, B, R=Me), epithilones, epristeride, estramustine analogue, estrogen agonists, estrogen antagonists, etanidazole, etoposide, etoposide 4'-phosphate (etopofos), exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, ganirelix, gelatinase inhibitors, gemcitabine, glutathione inhibitors, hepsulfam, heregulin, hexamethylene bisacetamide, homoharringtonine (HHT), hypericin, ibandronic acid idarubicin, idoxifene, idramantone, ilmofosine, ilomastat, imidazoacridones, imiquimod, immunostimulant peptides, insulin-like growth factor-1 receptor inhibitor, interferon agonists, interferons, interleukins, iobenguane, iododoxorubicin, ipomeanol, 4-, irinotecan, iroplact, irsogladine, isobengazole, isohomohalicondrin B, itasetron, jasplakinolide, kahalalide F, lamellarin-N triacetate, lanreotide, leinamycin, lenograstim, lentinan sulfate, leptolstatin, letrozole, leukemia inhibiting factor, leukocyte alpha interferon, leuprolide+estrogen+progesterone, leuprorelin, levamisole, liarozole, linear polyamine analogue, lipophilic disaccharide peptide, lipophilic platinum compounds, lissoclinamide 7, lobaplatin, lombricine, lometrexol, lonidamine, losoxantrone, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, menogaril, merbarone, meterelin, methioninase, metoclopramide, MIF inhibitor, mifepristone, miltefosine, mirimostim, mismatched double stranded RNA, mithracin, mitoguazone, mitolactol, mitomycin analogues, mitonafide, mitotoxin fibroblast growth factor-saporin, mitoxantrone, mofarotene, molgramostim, monoclonal antibody, human chorionic gonadotrophin, monophosphoryl lipid A+myobacterium cell wall sk, mopidamol, multiple drug resistance gene inhibitor, multiple tumor suppressor 1-based therapy, mustard anticancer agent, mycaperoxide B, mycobacterial cell wall extract, myriaporone, N-acetyldinaline, N-substituted benzamides, nafarelin, nagrestip, naloxone+pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, O6-benzylguanine, octreotide, okicenone, oligonucleotides, onapristone, ondansetron, ondansetron, oracin, oral cytokine inducer, ormaplatin, osaterone, oxaliplatin, oxaunomycin, paclitaxel analogues, paclitaxel derivatives, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, perillyl alcohol, phenazinomycin, phenylacetate, phosphatase inhibitors, picibanil, pilocarpine hydrochloride, pirarubicin, piritrexim, placetin A, placetin B, plasminogen activator inhibitor, platinum complex, platinum compounds, platinum-triamine complex, podophyllotoxin, porfimer sodium, porfiromycin, propyl bis-acridone, prostaglandin J2, proteasome inhibitors, protein A-based immune modulator, protein kinase C inhibitor, protein kinase C inhibitors, microalgal, protein tyrosine phosphatase inhibitors, purine nucleoside phosphorylase inhibitors, purpurins, pyrazoloacridine, pyridoxylated hemoglobin polyoxyethylene conjugate, raf antagonists, raltitrexed, ramosetron, ras farnesyl protein transferase inhibitors, ras inhibitors, ras-GAP inhibitor, retelliptine demethylated, rhenium Re 186 etidronate, rhizoxin, ribozymes, R11 retinamide, rogletimide, rohitukine, romurtide, roquinimex, rubiginone B1, ruboxyl, safingol, saintopin, SarCNU, sarcophytol A, sargramostim, Sdi 1 mimetics, semustine, senescence derived inhibitor 1, sense oligonucleotides, signal transduction inhibitors, signal transduction modulators, single chain antigen binding protein, sizofuran, sobuzoxane, sodium borocaptate, sodium phenylacetate, solverol, somatomedin binding protein, sonermin, sparfosic acid, spicamycin D, spiromustine, splenopentin, spongistatin 1, squalamine, stem cell inhibitor, stem-cell division inhibitors, stipiamide, stromelysin inhibitors, sulfinosine, superactive vasoactive intestinal peptide antagonist, suradista, suramin, swainsonine, synthetic glyobsaminoglycans, tallimustine, tamoxifen methiodide, tauromustine, tazarotene, tecogalan sodium, tegafur, tellurapyrylium, telomerase inhibitors, temoporfin, temozolomide, teniposide, tetrachlorodecaoxide, tetrazomine, thaliblastine, thalidomide, thiocoraline, thrombopoietin, thrombopoietin mimetic, thymalfasin, thymopoietin receptor agonist, thymotrinan, thyroid stimulating hormone, tin ethyl etiopurpurin, tirapazamine, titanocene dichloride, topotecan, topsentin, toremifene, totipotent stem cell factor, translation inhibitors, tretinoin, triacetyluridine, triciribine, trimetrexate, triptorelin, tropisetron, turosteride, tyrosine kinase inhibitors, tyrphostins, UBC inhibitors, ubenimex, urogenital sinus-derived growth inhibitory factor, urokinase receptor antagonists, vapreotide, variolin B, vector system, erythrocyte gene therapy, velaresol, veramine, verdins, verteporfin, vinorelbine, vinxaltine, vitaxin, vorozole, zanoterone, zeniplatin, zilascorb, and zinostatin stimalamer.

Other chemotherapeutic agents include: Antiproliferative agents (e.g., Piritrexim Isothionate), Antiprostatic hypertrophy agent (e.g., Sitogluside), Benign prostatic hyperplasia therapy agents (e.g., Tamsulosin Hydrochloride), Prostate growth inhibitor agents (e.g., Pentomone), and Radioactive agents: Fibrinogen I 125, Fludeoxyglucose F 18, Fluorodopa F 18, Insulin I 125, Insulin I 131, Iobenguane I 123, Iodipamide Sodium I 131, Iodoantipyrine I 131, Iodocholesterol I 131, Iodohippurate Sodium I 123, Iodohippurate Sodium I 125, Iodohippurate Sodium I 131, Iodopyracet I 125, Iodopyracet I 131, Iofetamine Hydrochloride I 123, Iomethin I 125, Iomethin I 131, Iothalamate Sodium I 125, Iothalamate Sodium I 131, Iotyrosine I 131, Liothyronine I 125, Liothyronine I 131, Merisoprol Acetate Hg 197, Merisoprol Acetate Hg 203, Merisoprol Hg 197, Methyl Iodobenzo Guanine (MIBG-I131 or MIBG-I123), Selenomethionine Se 75, Technetium Tc 99m Antimony Trisulfide Colloid, Technetium Tc 99m Bicisate, Technetium Tc 99m Disofenin, Technetium Tc 99m Etidronate, Technetium Tc 99m Exametazime, Technetium Tc 99m Furifosmin, Technetium Tc 99m Gluceptate, Technetium TC 99m Lidofenin, Technetium Tc 99m Mebrofenin, Technetium Tc 99m Medronate, Technetium Tc 99m Medronate Disodium, Technetium Tc 99m Mertiatide, Technetium Tc 99m Oxidronate, Technetium Tc 99m Pentetate, Technetium Tc 99m Pentetate Calcium Trisodium, Technetium Tc 99m Sestamibi, Technetium Tc 99m Siboroxime, Technetium Tc 99m Succimer, Technetium Tc 99m Sulfur Colloid, Technetium Tc 99m Teboroxime, Technetium Tc 99m Tetrofosmin, Technetium Tc 99m Tiatide, Thyroxine I 125, Thyroxine I 131, Tolpovidone I 131, Triolein I 125, and Triolein I 131. MIBG-I131 and MIBG-I123 are especially preferred chemotherapeutic agents for co-administration with the nitrofuran containing pharmaceutical compositions of the invention.

Another category of chemotherapeutic agents is anti-cancer Supplementary Potentiating Agents, including: Tricyclic anti-depressant drugs (e.g., imipramine, desipramine, amitryptyline, clomipramine, trimipramine, doxepin, nortriptyline, protriptyline, amoxapine and maprotiline), non-tricyclic anti-depressant drugs (e.g., sertraline, trazodone and citalopram), $Ca^{++}$ antagonists (e.g., verapamil, nifedipine, nitrendipine and caroverine), Calmodulin inhibitors (e.g., prenylamine, trifluoroperazine and clomipramine), Amphotericin B, Triparanol analogues (e.g., tamoxifen), antiarrhythmic drugs (e.g., quinidine), antihypertensive drugs (e.g., reserpine), Thiol depleters (e.g., buthionine and sulfoximine) and Multiple Drug Resistance reducing agents such as Cremaphor EL.

Other chemotherapeutic agents include: annonaceous acetogenins, asimicin, rolliniastatin, guanacone, squamocin, bullatacin, squamotacin, taxanes, paclitaxel, gemcitabine, methotrexate FR-900482, FK-973, FR-66979, FK-317, 5-FU, FUDR, FdUMP, Hydroxyurea, Docetaxel, discodermolide, epothilones, vincristine, vinblastine, vinorelbine, meta-pac, irinotecan, SN-38, 10-OH campto, topotecan, etoposide, adriamycin, flavopiridol, Cis-Pt, carbo-Pt, bleomycin, mitomycin C, mithramycin, capecitabine, cytarabine, 2-Cl-2' deoxyadenosine, Fludarabine-$PO_4$, mitoxantrone, mitozolomide, Pentostatin, and Tomudex.

One important class of chemotherapeutic agents are taxanes (e.g., paclitaxel and docetaxel). Nitrofuran compounds in combination with tamoxifen or aromatase inhibitor arimidex (i.e., anastrozole) are particularly useful for breast and gynecological cancers.

Examples antibodies that can be used as other active ingredients according to the invention include but are not limited to anti-CD20 mAb (monoclonal antibody), rituximab, Rituxan™, anti-CD20 mAb, tositumomab Bexxar, anti-HER2, trastuzumab, Herceptin™, anti-HER2, MDX-210, anti-CA125 mAb, oregovomab, B43.13, Ovarex™, Breva-Rex, AR54, GivaRex, ProstaRex, anti-EGF receptor mAb, IMC-C225, Erbitux™, anti-EGF receptor mAb, MDX-447, gemtuzumab ozogamicin, Mylotarg, CMA-676, anti-CD33 (Wyeth Pharmaceuticals), anti-tissue factor protein (TF), (Sunol), ior-c5, c5, anti-EGF receptor mAb, MDX-447, anti-17-1A mAb, edrecolomab, Panorex, anti-CD20 mAb (Y-90 labeled), ibritumomab tiuxetan (IDEC-Y2B8), Zevalin, anti-idiotypic mAb mimic of ganglioside GD3 epitope, BEC2, anti-HLA-Dr10 mAb (131 I LYM-1), Oncolym™, anti-CD33 humanized mAb (SMART M195), Zamyl™, anti-CD52 humAb (LDP-03), CAMPATH, anti-CD1 mAb, for t6, anti-CAR (complement activating receptor) mAb, MDX-11, humanized bispecific mAb conjugates (complement cascade activators), MDX-22, OV103 (Y-90 labeled antibody), celogovab, OncoScint™, anti-17-1A mAb, 3622W94, anti-VEGF (RhumAb-VEGF), bevacizumab, Avastin™, anti-TAC (IL-2 receptor) humanized Ab (SMART), daclizumab, Zenapax, anti-TAG-72 partially humanized bispecific Ab, MDX-220, anti-idiotypic mAb mimic of high molecular weight proteoglycan (I-Mel-I), MELIMMUNE-1, anti-idiotypic mAb mimic of high molecular weight proteoglycan (I-MeI-2), MELIMMUNE-2, anti-CEA Ab (hMN14), CEACide™, Pretarget™ radioactive targeting agents, hmAbH11 scFv fragment (NovomAb-G2), H11 scFv, anti-DNA or DNA-associated proteins (histones) mAb and conjugates, TNT (e.g. Cotara™), Gliomab-H mAb, GNI-250 mAb, anti-EGF receptor mAb, EMD-72000, anti-CD22 humanized Ab, LymphoCide, Non-Hodgkin's anti-CD33 mAb conjugate with calicheamicin (CMA 676), gemtuzumab ozogamicin, Mylotarg™, Monopharm-C, colon, anti-idiotypic human mAb to GD2 ganglioside, 4B5, melanoma, anti-EGF receptor humanized Ab, ior egf/r3, anti-ior c2 glycoprotein mAb, for c5, BABS (biosynthetic antibody binding site) proteins, anti-FLK-2/FLT-3 mAb, mAb/small-molecule conjugate, TAP (tumor-activated prodrug), anti-GD-2 bispecific mAb, MDX-260, antinuclear autoantibodies (binds nucleosomes), ANA Ab, anti-HLA-DR Ab (SMART 1D10 Ab), Remitogen™, SMART ABL 364 Ab, anti-CEA 1131-labeled mAb, ImmuRAIT-CEA.

Other antibodies that can be used according to the invention include anti-TNFα antibody such as infliximab (Remicade) and etanercept (Enbrel) for rheumatoid arthritis and Crohn's disease, palivizuma, anti-RSV antibody for pediatric subjects, bevacizumab, alemtuzumab, Campath-1H, BLyS-mAb, fSLE; anti-VEGF2, anti-Trail receptor; B3 mAb, m170 mAb, mAB BR96, and Abx-Cbl mAb. The invention embraces a number of classes of antibodies and fragments thereof including but not limited to antibodies directed to cancer antigens (as described above), cell surface molecule, stromal cell molecules, extracellular matrix molecules, and tumor vasculature associated molecules.

A cell surface molecule is a molecule that is expressed at the surface of a cell. In addition to an extracellular domain, it may further comprise a transmembrane domain and a cytoplasmic domain. Examples include HER 2, CD20, CD33, EGF receptor, HLA markers such as HLA-DR, CD52, CD1, CEA, CD22, GD2 ganglioside, FLK2/FLT3, VEGF, VEGFR, and the like.

A stromal cell molecule is a molecule expressed by a stromal cell. Examples include but are not limited to FAP and CD26.

An extracellular matrix molecule is a molecule found in the extracellular matrix. Examples include but are not limited to collagen, glycosaminoglycans (GAGs), proteoglycans, elastin, fibronectin and laminin.

A tumor vasculature associated molecule is a molecule expressed by vasculature of a tumor (i.e., a solid cancer rather than a systemic cancer such as leukemia). As with a cancer antigen, a tumor vasculature associated molecule may be expressed by normal vasculature however its presence on vasculature of a tumor makes it a suitable target for anti-cancer therapy. In some instances, the tumor vasculature associated molecule is expressed at a higher level in tumor vasculature than it is in normal vasculature. Examples include but are not limited to endoglin (see U.S. Pat. No. 5,660,827), ELAM-1, VCAM-1, ICAM-1, ligand reactive with LAM-1, MHC class II antigens, aminophospholipids such as phosphatidylserine and phosphatidylethanolamine (as described in U.S. Pat. No. 6,312,694), VEGFR1 (Flt-1) and VEGFR2 (KDR/Flk-1), and other tumor vasculature associated antigens such as those described in U.S. Pat. No. 5,776,427. Antibodies to endoglin are described in U.S. Pat. No. 5,660,827 and include TEC-4 and TEC-11, and antibodies that recognize identical epitopes to these antibodies. Antibodies to aminophospholipids are described in U.S. Pat. No. 6,312,694. Antibodies that inhibit VEGF are described in U.S. Pat. No. 6,342,219 and include 2C3 (ATCC PTA 1595). Other antibodies that are specific for tumor vasculature include antibodies that react to a complex of a growth factor and its receptor such as a complex of FGF and the FGFR or a complex of TGFβ and the TGFβR. Antibodies of this latter class are described in U.S. Pat. No. 5,965,132, and include GV39 and GV97.

It is to be understood that the antibodies embraced by the invention include those recited explicitly herein and also those that bind to the same epitope as those recited herein.

Also useful in the invention are antibodies such as the following, all of which are commercially available:

Apoptosis Antibodies:

BAX Antibodies: Anti-Human Bax Antibodies (Monoclonal), Anti-Human Bax Antibodies (Polyclonal), Anti-Murine Bax Antibodies (Monoclonal), Anti-Murine Bax Antibodies (Polyclonal);

Fas/Fas Ligand Antibodies: Anti-Human Fas/Fas Ligand Antibodies, Anti-Murine Fas/Fas Ligand Antibodies Granzyme Antibodies Granzyme B Antibodies;

BCL Antibodies: Anti Cytochrome C Antibodies, Anti-Human BCL Antibodies (Monoclonal), Anti-Human bcl Antibodies (Polyclonal), Anti-Murine bcl Antibodie, (Monoclonal), Anti-Murine bcl Antibodies (Polyclonal)

Miscellaneous Apoptosis Antibodies: Anti TRADD, TRAIL, TRAFF, DR3 Antibodies Anti-Human Fas/Fas Ligand Antibodies Anti-Murine Fas/Fas Ligand Antibodies;

Miscellaneous Apoptosis Related Antibodies: BIM Antibodies: Anti Human, Murine bim Antibodies (Polyclonal), Anti-Human, Murine bim Antibodies (Monoclonal);

PARP Antibodies: Anti-Human PARP Antibodies (Monoclonal), Anti-Human PARP Antibodies (Polyclonal) Anti-Murine PARP Antibodies;

Caspase Antibodies: Anti-Human Caspase Antibodies (Monoclonal), Anti-Murine Caspase Antibodies;

Anti-CD Antibodies: Anti-CD29, PL18-5 PanVera, Anti-CD29, PL4-3 PanVera, Anti-CD41a, PT25-2 PanVera, Anti-CD42b, PL52-4 PanVera, Anti-CD42b, GUR20-5 PanVera, Anti-CD42b, WGA-3 PanVeraAnti-CD43, 1D4 PanVera, Anti-CD46, MCP75-6 PanVera, Anti-CD61, PL11-7 PanVera, Anti-CD61, PL8-5 PanVera, Anti-CD62/P-slctn, PL7-6 PanVera, Anti-CD62/P-slctn, WGA-1 PanVera, Anti-CD154, 5F3 PanVera; and anti-CD1, anti-CD2, anti-CD3, anti-CD4, anti-CD5, anti-CD6, anti-CD7, anti-CD8, anti-CD9, anti-CD10, anti-CD11, anti-CD12, anti-CD13, anti-CD14, anti-CD15, anti-CD16, anti-CD17, anti-CD18, anti-CD19, anti-CD20, anti-CD21, anti-CD22, anti-CD23, anti-CD24, anti-CD25, anti-CD26, anti-CD27, anti-CD28, anti-CD29, anti-CD30, anti-CD31, anti-CD32, anti-CD33, anti-CD34, anti-CD35, anti-CD36, anti-CD37, anti-CD38, anti-CD39, anti-CD40 anti-CD41, anti-CD42, anti-CD43, anti-CD44, anti-CD45, anti-CD46, anti-CD47, anti-CD48, anti-CD49, anti-CD50, anti-CD51, anti-CD52, anti-CD53, anti-CD54, anti-CD55, anti-CD56, anti-CD57, anti-CD58, anti-CD59, anti-CD60, anti-CD61, anti-CD62, anti-CD63, anti-CD64, anti-CD65, anti-CD66, anti-CD67, anti-CD68, anti-CD69, anti-CD70, anti-CD71, anti-CD72, anti-CD73, anti-CD74, anti-CD75, anti-CD76, anti-CD77, anti-CD78, anti-CD79, anti-CD80, anti-CD81, anti-CD82, anti-CD83, anti-CD84, anti-CD85, anti-CD86, anti-CD87, anti-CD88, anti-CD89, anti-CD90, anti-CD91, anti-CD92, anti-CD93, anti-CD94, anti-CD95, anti-CD96, anti-CD97, anti-CD98, anti-CD99, anti-CD100, anti-CD101, anti-CD102, anti-CD103, anti-CD104, anti-CD105, anti-CD106, anti-CD107, anti-CD108, anti-CD109, anti-CD110, anti-CD111, anti-CD112, anti-CD113, anti-CD114, anti-CD115, anti-CD116, anti-CD117, anti-CD118, anti-CD119, anti-CD120, anti-CD121, anti-CD122, anti-CD123, anti-CD124, anti-CD125, anti-CD126, anti-CD127, anti-CD128, anti-CD129, anti-CD130, anti-CD131, anti-CD132, anti-CD133, anti-CD134, anti-CD135, anti-CD136, anti-CD137, anti-CD138, anti-CD139, anti-CD140, anti-CD141, anti-CD142, anti-CD143, anti-CD144, anti-CD145, anti-CD146, anti-CD147, anti-CD148, anti-CD149, anti-CD150, anti-CD151, anti-CD152, anti-CD153, anti-CD154, anti-CD155, anti-CD156, anti-CD157, anti-CD158, anti-CD159, anti-CD160, anti-CD161, anti-CD162, anti-CD163, anti-CD164, anti-CD165, anti-CD166, anti-CD167, anti-CD168, anti-CD169, anti-CD170, anti-CD171, anti-CD172, anti-CD173, anti-CD174, anti-CD175, anti-CD176, anti-CD177, anti-CD178, anti-CD179, anti-CD180, anti-CD181, anti-CD182, anti-CD183, anti-CD184, anti-CD185, anti-CD186, anti-CD187, anti-CD188, anti-CD189, anti-CD190, anti-CD191, anti-CD192, anti-CD193, anti-CD194, anti-CD195, anti-CD196, anti-CD197, anti-CD198, anti-CD199, anti-CD200, anti-CD201, anti-CD202, anti-CD203, anti-CD204, anti-CD265, anti-CD206, anti-CD207, anti-CD208, anti-CD209, anti-CD210, anti-CD211, anti-CD212, anti-CD213, anti-CD214, anti-CD215, anti-CD216, anti-CD217, anti-CD218, anti-CD219, anti-CD220, anti-CD221, anti-CD222, anti-CD223, anti-CD224, anti-CD225, anti-CD226, anti-CD227, anti-CD228, anti-CD229, anti-CD230, anti-CD231, anti-CD232, anti-CD233, anti-CD234, anti-CD235, anti-CD236, anti-CD237, anti-CD238, anti-CD239, anti-CD240 anti-CD241, anti-CD242, anti-CD243, anti-CD244, anti-CD245, anti-CD246, anti-CD247, anti-CD248, anti-CD249, anti-CD250, and the like.

Human Chemokine Antibodies: Human CNTF Antibodies, Human Eotaxin Antibodies, Human Epitherlial Neutrophil Activating Peptide-78, Human Exodus Antibodies, Human GRO Antibodies, Human HCC-1 Antibodies, Human 1-309 Antibodies, Human IP-10 Antibodies, Human I-TAC Antibodies, Human LIF Antibodies, Human Liver-Expressed Chemokine Antibodies, Human lymphotoxin Antibodies, Human MCP Antibodies, Human MIP Antibodies, Human Monokine Induced by IFN-gamma Antibodies, Human NAP-2 Antibodies, Human NP-1 Antibodies, Human Platelet Factor-4 Antibodies, Human RANTES Antibodies, Human SDF Antibodies, Human TECK Antibodies;

Murine Chemokine Antibodies: Human B-Cell Attracting Murine Chemokine Antibodies, Chemokine-1 Antibodies, Murine Eotaxin Antibodies, Murine Exodus Antibodies, Murine GCP-2 Antibodies, Murine KC Antibodies, Murine MCP Antibodies, Murine MIP Antibodies, Murine RANTES Antibodies, Rat Chemokine Antibodies, Rat Chemokine Antibodies, Rat CNTF Antibodies, Rat GRO Antibodies, Rat MCP Antibodies, Rat MIP Antibodies, Rat RANTES Antibodies;

Cytokine/Cytokine Receptor Antibodies: Human Biotinylated Cytokine/Cytokine Receptor Antibodies, Human IFN Antibodies, Human IL Antibodies, Human Leptin Antibodies, Human Oncostatin Antibodies, Human TNF Antibodies, Human TNF Receptor Family Antibodies, Murine Biotinylated Cytokine/Cytokine Receptor Antibodies, Murine IFN Antibodies, Murine IL Antibodies, Murine TNF Antibodies, Murine TNF Receptor Antibodies; anti-CCR4 antibody;

Rat Cytokine/Cytokine Receptor Antibodies: Rat Biotinylated Cytokine/Cytokine Receptor Antibodies, Rat IFN Antibodies, Rat IL Antibodies, Rat TNF Antibodies;

ECM Antibodies: Collagen/Procollagen, Laminin, Collagen (Human), Laminin (Human), Procollagen (Human), Vitronectin/Vitronectin Receptor, Vitronectin (Human), Vitronectin Receptor (Human), Fibronectin/Fibronectin Receptor, Fibronectin (Human), Fibronectin Receptor (Human);

Growth Factor Antibodies: Human Growth Factor Antibodies, Murine Growth Factor Antibodies, Porcine Growth Factor Antibodies;

Miscellaneous Antibodies: B aculovirus Antibodies, Cadherin Antibodies, Complement Antibodies, Clq Antibodies, VonWillebrand Factor Antibodies, Cre Antibodies, HIV Antibodies, Influenza Antibodies, Human Leptin. Antibodies, Murine Leptin Antibodies, Murine CTLA-4 Antibodies, Human CTLA-4 Antibodies, P450 Antibodies, RNA Polymerase Antibodies;

Neurobio Antibodies: Amyloid Antibodies, GFAP Antibodies, Human NGF Antibodies, Human NT-3 Antibodies, Human NT-4 Antibodies:

Still other antibodies can be used in the invention and these include antibodies listed in references such as the MSRS Catalog of Primary Antibodies, and Linscott's Directory.

In some preferred embodiments of the invention, the antibodies are Avastin (bevacizumab), BEC2 (mitumomab), Bexxar (tositumomab), Campath (alemtuzumab), CeaVac, Herceptin (trastuzumab), IMC-C225 (centuxitmab), LymphoCide (epratuzumab), MDX-210, Mylotarg (gemtuzumab ozogamicin), Panorex (edrecolomab), Rituxan (rituximab), Theragyn (pemtumomab), Zamyl, and Zevalin (ibritumomab tituxetan). The invention also covers antibody fragments thereof.

In some preferred embodiments, the cancer antigen is VEGF, Anti-idiotypic mAb (GD3 ganglioside mimic), CD20, CD52; Anti-idiotypic mAb (CEA mimic), ERBB2, EGFR, CD22, ERBB2 X CD65 (fcyRl), EpCam, PEM and CD33.

The invention encompasses the use of both antibodies and antibody fragments. The antibodies may be monoclonal or polyclonal, and can be prepared by conventional methodology. They may further be isolated or present in an ascites fluid. Such antibodies can be further manipulated to create chimeric or humanized antibodies as will be discussed in greater detail below.

Significantly, as is well-known in the art, only a small portion of an antibody molecule, the paratope, is involved in the binding of the antibody to its epitope (see, in general, Clark, W. R. (1986) The Experimental Foundations of Modern Immunology Wiley & Sons, Inc., New York; Roitt, I. (1991) Essential Immunology, 7th Ed., Blackwell Scientific Publications, Oxford). The pFc' and Fc regions, for example, are effectors of the complement cascade but are not involved in antigen binding. An antibody from which the pFc', region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of co-specific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions has been replaced by FR regions of human origin. Such antibodies, including fragments of intact antibodies with antigen-binding ability, are often referred to as "chimeric" antibodies. Commercial sources of humanized or chimeric antibodies include GenPharm, Xenotech, AbGenix and CellGeneSys.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

The nitrofuran compounds are administered in therapeutically effective and physiologically acceptable amounts, which is the amount physiologically tolerable to the subject that is necessary or sufficient to realize the desired beneficial biologic effect, in this case the treatment of cancer or the inhibition of angiogenesis. A biologically beneficial effect can, for example, be measured by determining the physiological effects of the treatment following administration of the treatment. The biologically beneficial effect may be the amelioration and or absolute elimination of symptoms resulting from the disorder being treated, or the inhibition of angiogenesis in the disorder being treated as evidenced, for example, by a reduction in the number of microvessels (e.g., abnormal microvessels) on imaging.

The therapeutically effective and physiologically acceptable amount may vary depending upon the particular compound(s) or combination of compounds and/or therapies used. It can also vary depending on such factors as the condition (e.g. cancer) being treated, the size of the subject, or the severity of the disease or condition. One of ordinary skill in the art can empirically determine the effective amount of a particular nitrofuran compound or combination without necessitating undue experimentation. Combined with the teachings provided herein, by choosing among the various compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject.

In some instances, a sub-therapeutic dosage of either the nitrofuran compound or the second agent, or a sub-therapeutic dosage of both, is used to treat the subject. For example, when a nitrofuran compound is used together with an anti-cancer agent, the nitrofuran compound and the anti-cancer agent may be administered in sub-therapeutic doses and still produce a desirable therapeutic effect. A "sub-therapeutic dose" as used herein refers to a dosage which is less than that dosage which would produce a therapeutic result in the subject if administered in the absence of the other agent. Thus, the sub-therapeutic dose of an anti-cancer agent is one which would not produce the same or a substantially similar therapeutic result in the subject in the absence of the administration of nitrofuran compound. Therapeutic doses of anti-cancer agents are known in the field of medicine. These doses have been extensively described in references such as Remington's Pharmaceutical Sciences, 18th ed., 1990, or the Physician Desktop Reference; as well as many other medical references relied upon by the medical profession as guidance for the treatment of cancer and are well known in the art.

For any compound described herein a therapeutically effective amount may be initially determined from in vitro assays such as cell culture assays. Therapeutically effective amounts can also be determined in animal studies. For instance, the effective amount of a nitrofuran compound with or without a second agent can be assessed using in vivo assays of, for example, tumor regression and/or prevention of tumor formation. Relevant animal models include, for example, assays in which malignant cells are injected into the animal subjects, usually in a defined site. Generally, a range of nitrofuran compound doses are administered into the animal. Inhibition of the growth of a tumor following the injection of the malignant cells is indicative of the ability to reduce the risk of developing a cancer. Inhibition of further growth (or reduction in size) of a pre-existing tumor is indicative of the ability to treat the cancer.

The applied dose of both agents can be adjusted based on the relative bioavailability and potency of the administered compound(s). Adjusting the dose to achieve maximal efficacy based on the methods described above and other methods are well within the capabilities of the ordinarily skilled artisan.

Subject doses of the compounds described herein typically range from about 0.1 µg to 30,000 mg, more typically from about 1 µg/day to 20,000 mg, even more typically from about 10 µg to 15,000 mg, and most typically from about 100 µg to 10,000 Stated in terms of subject body weight, typical dosages range from about 0.1 µg to 200 mg/kg/day, more typically from about 0.5 to 150 mg/kg/day. In some important embodiments, the compound is administered in amounts from about 1 to 100 mg/kg/day. In some other important embodiments, the compound is administered in an amount of 10-60 mg/kg/day.

A "routine schedule" as used herein, refers to a predetermined designated period of time. The routine schedule may encompass periods of time which are identical or which differ in length, as long as the schedule is predetermined. For instance, the routine schedule may involve 2, 3, 4, or 6 administrations per day, administration on a daily basis, every two days, every three days, every four days, every five days, every six days, a weekly basis, a monthly basis or any set number of days or weeks there-between, every two months, three months, four months, five months, six months, seven months, eight months, nine months, ten months, eleven months, twelve months, etc. Alternatively, the predetermined routine schedule may involve administration on a daily basis for the first week, followed by a monthly basis for several months, and then every three months after that. Any particular combination would be covered by the routine schedule as long as it is determined ahead of time that the appropriate schedule involves administration on a certain day.

The compounds of the invention may be administered in pharmaceutically acceptable carriers, or in the context of a vector or delivery system. An example of a chemical/physical vector of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2-4.0 µm can encapsulate large macromolecules. RNA, DNA and intact virions can be encapsulated within the aqueous interior and be delivered to cells in a biologically active form (Fraley, et al., *Trends Biochem. Sci.*, (1981) 6:77).

Liposomes may be targeted to a particular tissue by coupling the liposome to a specific ligand such as a sugar, glycolipid, or protein. Ligands which may be useful for targeting a liposome to a cell include, but are not limited to intact or fragments of molecules which interact with cell specific receptors and molecules, such as antibodies, which interact with the cell surface markers of cells. Such ligands may easily be identified by binding assays well known to those of skill in the art. In still other embodiments, the liposome may be targeted to the cancer by coupling it, for example, to one of the immunotherapeutic antibodies discussed earlier. Additionally, the vector may be coupled to a nuclear targeting peptide, which will direct the vector to the nucleus of the host cell.

Liposomes are commercially available from Gibco BRL, for example, as LIPOFECTIN™ and LIPOFECTACET™, which are formed of cationic lipids such as N-[1-(2, 3 dioleyloxy)-propyl]-N,N, N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in *Trends in Biotechnology*, (1985) 3:235-241.

In another embodiment, the chemical/physical vector is a biocompatible microsphere that is suitable for delivery, such as oral or mucosal delivery. Such microspheres are disclosed in Chickering et al., *Biotech. And Bioeng.*, (1996) 52:96-101 and Mathiowitz et al., *Nature*, (1997) 386:410-414 and PCT Patent Application WO97/03702.

Both non-biodegradable and biodegradable polymeric matrices can be used to deliver the nitrofuran compound and/or the second agent to the subject. Biodegradable matrices are preferred. Such polymers may be natural or synthetic polymers. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multi-valent ions or other polymers.

The polymeric matrix preferably is in the form of a microparticle such as a microsphere (wherein the agents are dispersed throughout a solid polymeric matrix) or a microcapsule (wherein the agents are stored in the core of a polymeric shell). Other forms of the polymeric matrix for containing the agents include films, coatings, gels, implants, and stents. The size and composition of the polymeric matrix device is selected to result in favorable release kinetics in the tissue into which the matrix is introduced. The size of the polymeric matrix further is selected according to the method of delivery which is to be used, typically injection into a tissue or administration of a suspension by aerosol into the nasal and/or pulmonary areas. Preferably when an aerosol route is used the polymeric matrix and the nitrofuran compound are encompassed in a surfactant vehicle. The polymeric matrix composition can be selected to have both favorable degradation rates and also to be formed of a material which is bioadhesive, to further increase the effectiveness of transfer when the matrix is administered to a nasal and/or pulmonary surface that has sustained an injury. The matrix composition also can be selected not to degrade, but rather, to release by diffusion over an extended period of time. In some preferred embodiments, the nitrofuran compound is administered to the subject via an implant.

Bioadhesive polymers of particular interest include bioerodible hydrogels described by H. S. Sawhney, C. P. Pathak and J. A. Hubell in *Macromolecules*, (1993) 26:581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(laurel methacrylate), poly(phenyl methacrylate), poly(methyl acrylate), poly(isopropyl acrylate), poly(isobutyl acrylate), and poly(octadecyl acrylate).

The compositions and methods of the invention in certain instances may be useful for replacing existing surgical procedures or drug therapies, although in most instances the present invention is useful in improving the efficacy of existing therapies for treating such conditions. Accordingly combination therapy may be used to treat the subjects that are undergoing or that will undergo a treatment for cancer. For example, the agents may be administered to a subject in combination with another anti-proliferative (e.g., an anti-cancer) therapy. Suitable anti-cancer therapies include surgical procedures to remove the tumor mass, chemotherapy or localized radiation. The other anti-proliferative therapy may be administered before, concurrent with, or after treatment with the agent of the invention. There may also be a delay of several hours, days and in some instances weeks between the administration of the different treatments, such that the agent may be administered before or after the other treatment. In some embodiments, the nitrofuran compound may be administered with or without the other anti-proliferative treatment (e.g., prior to surgery, radiation or chemotherapy), although the timing is not so limited.

The nitrofuran compound can also be administered in combination with non-surgical, anti-proliferative (e.g., anti-cancer) drug therapy. In one embodiment, the agent may be administered in combination with an anti-cancer agent such as a cytostatic compound. A cytostatic compound is a compound (e.g., a nucleic acid, a protein) that suppresses cell growth and/or proliferation. In some embodiments, the cytostatic compound is directed towards the malignant cells of a tumor. In yet other embodiments, the cytostatic compound is one which inhibits the growth and/or proliferation of vascular smooth muscle cells or fibroblasts.

According to the methods of the invention, the nitrofuran or nitrofuran analog may be administered prior to, concurrent with, or following other anti-cancer agent(s). The administration schedule may involve administering the different agents in an alternating fashion. In other embodiments, the combination therapy of the invention may be delivered before and during, or during and after, or before and after treatment with other therapies. In some cases, the agent is administered more than 24 hours before the administration of the other anti-proliferative treatment. In other embodiments, more than one anti-proliferative therapy may be administered to a subject. For example, the subject may receive the agents of the invention, in combination with both surgery and at least one other anti-proliferative compound. Alternatively, the agent may be administered in combination with more than one anti-cancer agent.

The nitrofuran compound can be combined with other therapeutic agents such as adjuvants to enhance immune responses. The nitrofuran or nitrofuran analog and other therapeutic agent(s) may be administered simultaneously or sequentially. When the other therapeutic agents are administered simultaneously they can be administered in the same or separate formulations, but are administered at the same time. The administration of the other therapeutic agents and the nitrofuran or nitrofuran analog can also be temporally separated, meaning that the therapeutic agents are administered at a different time, either before or after, the administration of the nitrofuran or nitrofuran analog. The separation in time between the administration of these compounds and agents may be a matter of minutes or it may be longer. Other therapeutic agents include but are not limited to nucleic acid adjuvants, non-nucleic acid adjuvants, cytokines, non-immunotherapeutic antibodies, antigens, etc.

A nucleic acid adjuvant is an adjuvant that is a nucleic acid. Examples include immunostimulatory nucleic acid molecules such as those containing CpG dinucleotides, as described in U.S. Patents U.S. Pat. No. 6,194,388 B1, issued Feb. 27, 2001, U.S. Pat. No. 6,207,646 B1, issued Mar. 27, 2001, and U.S. Pat. No. 6,239,116 B1, issued May 29, 2001.

A "non-nucleic acid adjuvant" is any molecule or compound except for the immunostimulatory nucleic acids described herein which can stimulate the humoral and/or cellular immune response. Non-nucleic acid adjuvants include, for instance, adjuvants that create a depo effect, immune-stimulating adjuvants, adjuvants that create a depo effect and stimulate the immune system and mucosal adjuvants.

An "adjuvant that creates a depo effect" as used herein is an adjuvant that causes an antigen, such as a cancer antigen present in a cancer vaccine, to be slowly released in the body, thus prolonging the exposure of immune cells to the antigen. This class of adjuvants includes but is not limited to alum (e.g., aluminum hydroxide, aluminum phosphate); or emulsion-based formulations including mineral oil, non-mineral oil, water-in-oil or oil-in-water-in oil emulsion, oil-in-water emulsions such as Seppic ISA series of Montanide adjuvants (e.g., Montanide ISA 720, AirLiquide, Paris, France); MF-59 (a squalene-in-water emulsion stabilized with Span 85 and Tween 80; Chiron Corporation, Emeryville, Calif.; and PROVAX (an oil-in-water emulsion containing a stabilizing detergent and a micelle-forming agent; IDEC Pharmaceuticals Corporation, San Diego, Calif.).

An "immune stimulating adjuvant" is an adjuvant that causes activation of a cell of the immune system. It may, for instance, cause an immune cell to produce and secrete cytokines. This class of adjuvants includes but is not limited to saponins purified from the bark of the *Q. saponaria* tree, such as QS21 (a glycolipid that elutes in the 21$^{st}$ peak with HPLC fractionation; Antigenics, Inc., Waltham, Mass.); poly [di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.).

"Adjuvants that create a depo effect and stimulate, the immune system" are those compounds which have both of the above-identified functions. This class of adjuvants includes but is not limited to ISCOMS (Immunostimulating complexes which contain mixed saponins, lipids and form virus-sized particles with pores that can hold antigen; CSL, Melbourne, Australia); SB-AS2 (SmithKline Beecham adjuvant system #2 which is an oil-in-water emulsion containing MPL and QS21: SmithKline Beecham Biologicals [SBB], Rixensart, Belgium); SB-AS4 (SmithKline Beecham adjuvant system #4 which contains alum and MPL; SBB, Belgium); nonionic block copolymers that form micelles such as CRL 1005 (these contain a linear chain of hydrophobic polyoxypropylene flanked by chains of polyoxyethylene; Vaxcel, Inc., Norcross, Ga.); and Syntex Adjuvant Formulation (SAF, an oil-in-water emulsion containing Tween 80 and a nonionic block copolymer; Syntex Chemicals, Inc., Boulder, Colo.).

A "non-nucleic acid mucosal adjuvant" as used herein is an adjuvant other than an immunostimulatory nucleic acid that is capable of inducing a mucosal immune response in a subject when administered to a mucosal surface in conjunction with an antigen. Mucosal adjuvants include but are not limited to Bacterial toxins: e.g., Cholera toxin (CT), CT derivatives including but not limited to CT B subunit (CTB) (Wu et al., 1998, Tochikubo et al., 1998); CTD53 (Val to Asp) (Fontana et al., 1995); CTK97 (Val to Lys) (Fontana et al., 1995); CTK104 (Tyr to Lys) (Fontana et al., 1995); CTD53/K63 (Val to Asp, Ser to Lys) (Fontana et al., 1995); CTH54 (Arg to His) (Fontana et al., 1995); CTN107 (H is to Asn) (Fontana et al., 1995); CTE114 (Ser to Glu) (Fontana et al., 1995); CTE112K (Glu to Lys) (Yamamoto et al., 1997a); CTS61F (Ser to Phe) (Yamamoto et al., 1997a, 1997b); CTS106 (Pro to Lys) (Douce et al., 1997, Fontana et al., 1995); and CTK63 (Ser to Lys) (Douce et al., 1997, Fontana et al., 1995), Zonula occludens toxin, zot, *Escherichia coli* heat-labile enterotoxin, Labile Toxin (Li), LT derivatives including but not limited to LT B subunit (LTB) (Verweij et al., 1998); LT7K (Arg to Lys) (Komase et al., 1998, Douce et al., 1995); LT61F (Ser to Phe) (Komase et al., 1998); LT112K (Glu to Lys) (Komase et al., 1998); LT118E (Gly to Glu) (Komase et al., 1998); LT146E (Arg to Glu) (Komase et al., 1998); LT192G (Arg to Gly) (Komase et al., 1998); LTK63 (Ser to Lys) (Marchetti et al., 1998, Douce et al., 1997, 1998, Di Tommaso et al., 1996); and LTR72 (Ala to Arg) (Giuliani et al., 1998), Pertussis toxin, PT. (Lycke et al., 1992, Spangler B D, 1992, Freytag and Clemments, 1999, Roberts et al., 1995, Wilson et al.; 1995) including PT-9K/129G (Roberts et al., 1995, Cropley et al., 1995); Toxin derivatives (see below) (Holmgren et al., 1993, Verweij et al., 1998, Rappuoli et al., 1995, Freytag and Clements, 1999); Lipid A derivatives (e.g., monophosphoryl lipid A, MPL) (Sasaki et al., 1998, Vancott et al., 1998); Muramyl Dipeptide (MDP) derivatives (Fukushima et al., 1996, Ogawa et al., 1989, Michalek et al., 1983, Morisaki et al., 1983); Bacterial outer membrane proteins (e.g., outer surface protein A (OspA) lipoprotein of *Borrelia burgdorferi*, outer membrane protein of *Neisseria meningitidis*) (Mannaro et al., 1999, Van de Verg et al., 1996); Oil-in-water emulsions (e.g., MF59) (Barchfield et al., 1999, Verschoor et al., 1999, O'Hagan, 1998); Aluminum salts (Isaka et al., 1998, 1999); and Saponins (e.g., QS21) Aquila Biopharmaceuticals, Inc., Worcester, Mass.) (Sasaki et al., 1998, MacNeal et al., 1998), ISCOMS, MF-59 (a squalene-in-water emulsion stabilized with Span 85 and Tween 80; Chiron Corporation, Emeryville, Calif.); the Seppic ISA series of Montanide adjuvants (e.g., Montanide ISA 720; AirLiquide, Paris, France); PROVAX (an oil-in-water emulsion containing a stabilizing detergent and a micell-forming agent; IDEC Pharmaceuticals Corporation, San Diego, Calif.); Syntext Adjuvant Formulation (SAF; Syntex Chemicals, Inc., Boulder, Colo.); poly[di(carboxylatophenoxy)phosphazene (PCPP polymer; Virus Research Institute, USA) and *Leishmania* elongation factor (Corixa Corporation, Seattle, Wash.).

The invention further provides kits that comprise the compounds and/or agents of the invention and optionally instructions of use thereof. The compounds and/or agents may be present in parenteral forms (e.g., for intravenous, intramuscular, or intrathecal administration) or in oral forms such as tablets, pills, capsules, caplets and the like. The kit may further contain a second active ingredient or agent either formulated together with the nitrofuran or formulated separately. The unit dosages provided in each form will depend upon whether the nitrofuran compound is used together with or in the absence of the second ingredient or agent. The kit may optionally comprise a housing such as a box or a bag. Instructions for use may be supplied separately from the dispensing unit or housing or they may be imprinted on one or both. The compounds and/or agents may be provided in a one a day dispensing unit such as a blister pack or dial pack type dispenser, preferably with days of the week or day of the month (e.g., 1, 2, 3, 4, etc.) printed on the dispenser. If the compounds and/or agents are to be administered every other day or twice (or more) a day, the dispensing unit can be modified accordingly.

Figure 2A:
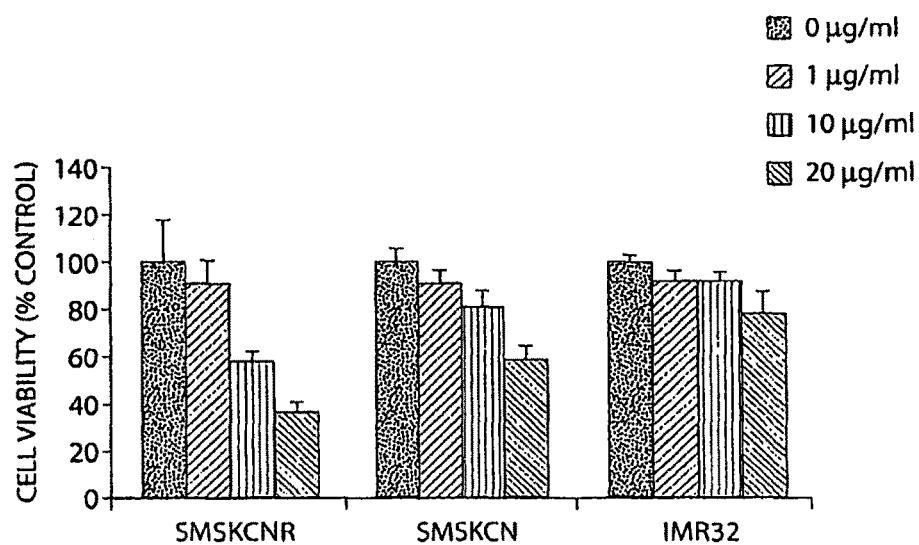
FIG. 2A is a histogram showing cell viability of neuroblastoma cells at different doses of nifurtimox. Cell viability assay: SMS-KCN, SMS-KCNR, and IMR-32 cells were cultured in 48 well plates (50,000 cells/well) and treated with 1 μg/ml, 10 μg/ml or 20 μg/ml of Nifurtimox for 120 hours. Cell viability was assessed using the MTS assay as described in Materials and Methods and expressed as percent of vehicle treated control. The data represents the mean±SD of four replicates.
Figure 3A:
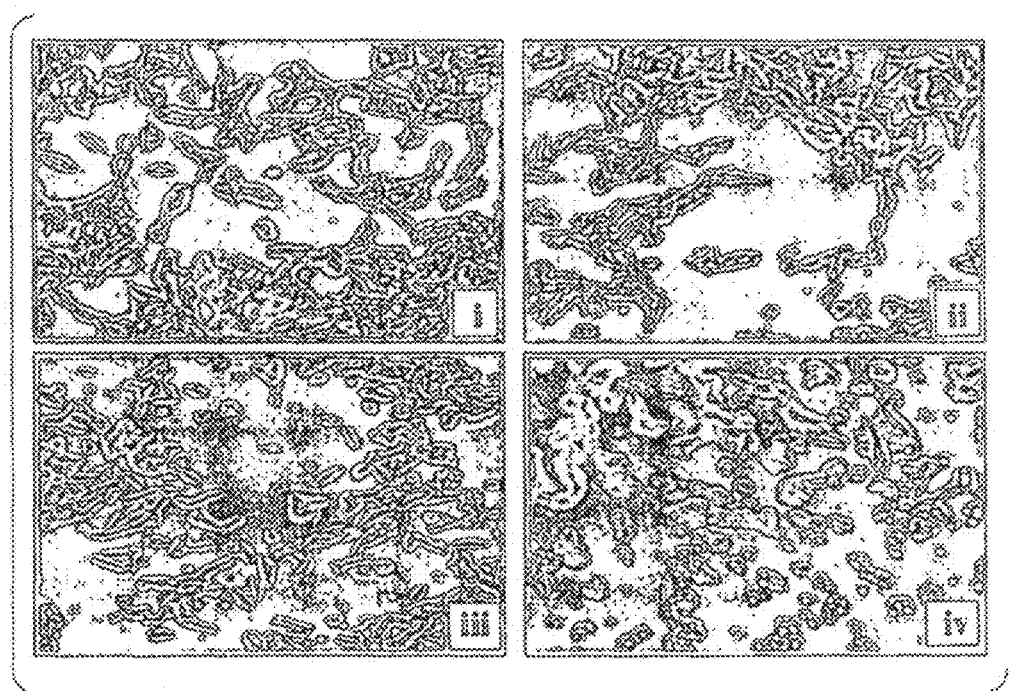
FIG. 3A is a set of photographs showing the effect of nifurtimox on neuroblastoma cells. Sub-confluent cultures of SMS-KCNR cells were treated with 0, 1.0, 10 and 20 μg/ml nifurtimox for 96 hours. The cells were photographed using a light microscope as described in Materials and Methods at ×100 magnification. Vehicle treated cells were used as control. Panels i: Vehicle control, ii: 1 μg/ml, iii: 10 μg/ml, and iv: 20 μg/ml nifurtimox.

The following examples are provided to illustrate specific instances of the practice of the present invention. They are not intended to limit the scope of the invention. As will be apparent to one of ordinary skill in the art, the present invention will find application in a variety of methods and compositions. In the examples, the therapeutic potential of nifurtimox on neuroblastoma using three neuroblastoma cell lines (SMS-KCNR, SMS-KCN, and IMR-32) which are representative of the Type 3 childhood form of neuroblastom[16], is demonstrated. Without intending to be bound by any particular theory, it is believed that the molecular mechanism of action of nifurtimox involves formation of free radicals within cells[9,17]. Cellular damage caused by free radicals result in induction of apoptosis leading to the observed toxicity by nifurtimox[18-20]. Earlier studies have shown that the treatment of *T. cruzi* epimastigotes with nifurtimox decreased cell viability which was associated with increased ultrastructural damage in the cell[10,21]. A similar cytotoxic effect was observed by nifurtimox on SMS-KCNR, SMS-KCN and IMR-32 neuroblastoma cell lines as described in Example 4. Among the different neuroblastoma cell lines used, SMS-KCNR was found to be most sensitive to nifurtimox and further studies were carried out using this cell line. Nifurtimox showed a dose and time dependent decrease in cell viability (FIG. 2A). Decrease in cell viability may be due to cell death due to cytotoxicity of the drug or lack of proliferation. Our studies demonstrated dose dependent decrease in cell proliferation using BrdU assay as detailed in Example 5. The cytotoxic effect of nifurtimox was evident during microscopic examination as described in Example 6, during which, the cells were found to be rounding up and floating suggestive of apoptosis (FIG. 3A). TUNEL assay was performed to confirm apoptosis. In this assay, the DNA termini generated following fragmentation, as in the case of apoptosis, were labeled with fluorescent deoxy-thymidine analog using the terminal deoxynucleotide transferase enzyme. Increased number of terminal ends in the DNA leads to increased labeling which in turn is reflected in the increased fluorescence signal[22]. Increased TUNEL staining was observed with nifurtimox treatment (FIG. 3B) which indicated that the drug caused apoptosis in the neuroblastoma cells.

Figure 4A:
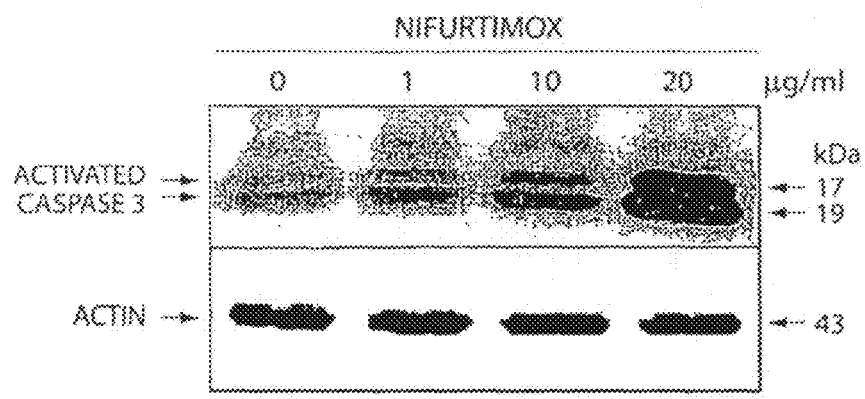
FIG. 4A is a picture of a slot showing the effect of nifurtimox in caspase-3 activation in neuroblastoma cells. SMS-KCNR cells were cultured and incubated with increasing concentrations of nifurtimox for 96 hours. The cells were lysed, separated on 12% SDS PAGE, blotted on to PVDF membrane and probed with antibodies specific for activated caspase-3 as described in the Example. The blots were stripped and reprobed with actin antibodies as loading control. Upper panel—Activated Caspase-3, Lower panel—Actin.

Caspases are a central component of apoptotic machinery and caspase-3 is an executioner caspase that is activated by several anti-cancer drugs[23]. As detailed in Example 9, upon treatment with nifurtimox, there was strong activation of caspase-3. This is shown by an immunoblot of treated cells with antibodies specific to activated caspase-3 (FIG. 4A). Caspase-3 activation was dose dependent which corresponded with increased apoptosis marked by increased TUNEL staining of the treated cells.

Figure 4B:
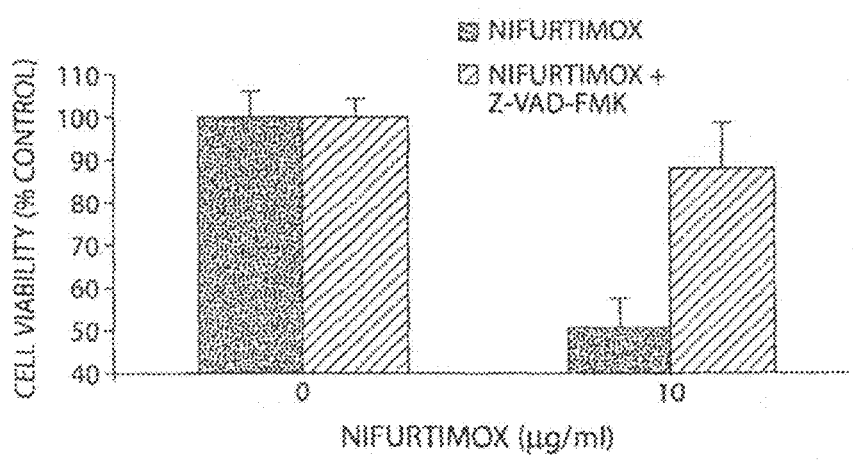
FIG. 4B is a histogram showing the effect of nifurtimox on neuroblastoma cell viability in the absence or presence of Z-VAD-FMK. SMS-KCNR cells were pretreated with pancaspase inhibitor, Z-VAD-FMK. SMS-KCNR cells were pretreated with 50 μM Z-VAD-FMK for 90 minutes before treatment with nifurtimox (10 μg/ml) for 96 hours. Cell viability was measured by MTS assay. The reversal of cytotoxicity by pancaspase inhibitor was determined by comparing the viability of nifurtimox treated cells in the presence or absence of the pancaspase inhibitor. The values are the mean±SD of quadruplicates.
Figure 5A:
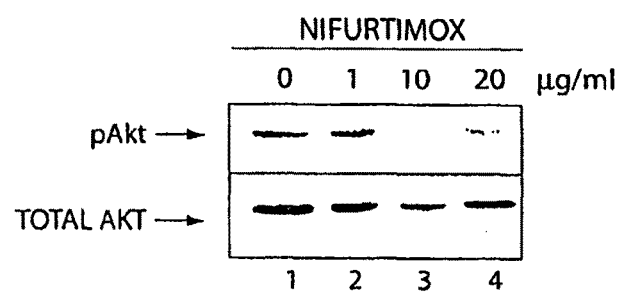
FIG. 5 is a picture of a Western Blot showing the effect of nifurtimox on Akt Phosphorylation. (A): SMS-KCNR cells were serum deprived for 18 hours, treated with 0, 1.0, 10 and 20 μg/ml nifurtimox for 90 minutes and then stimulated with BDNF (100 μg/ml) for 10 minutes. Cells were lysed and analyzed by western blot analysis using phospho-Akt antibodies (upper panel). The blots were stripped and reprobed with antibodies specific for total Akt protein (lower panel). (B): SMS-KCNR cells were treated with nifurtimox for 90 minutes in the presence of serum. Cells were then lysed and analyzed by western blot analysis using antibodies.
Figure 5B:
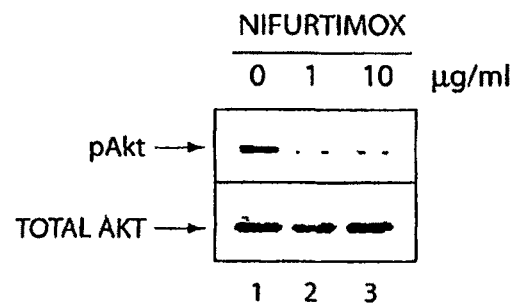

The role of caspases in the nifurtimox induced apoptosis was corroborated by using caspase inhibitors. Pretreatment of cells with Z-VAD-FMK, a pan-caspase inhibitor[24], which has the ability to inhibit a broad range of caspases effectively, reversed nifurtimox induced apoptosis in the neuroblastoma cells (FIG. 4B). This reversal of apoptosis by Z-VAD-FMK confirmed the involvement of caspases in the nifurtimox induced apoptosis of neuroblastoma cells. The pan-caspase inhibitor, Z-VAD-FMK, has been used by others to confirm caspase mediated apoptosis by Flavopiridol treated neuroblastoma cell lines[25].

Figure 6A:
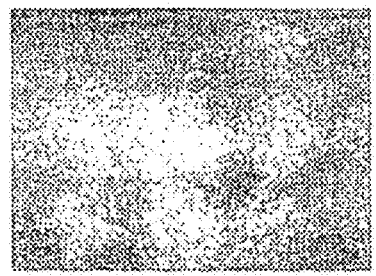
FIG. 6 is a set of pictures showing the inhibition of angiogenesis by nifurtimox on microvascular sprouting in growth factor stimulated aortic ring assay. (A) Vehicle treated aorta without growth factor (B) Vehicle treated aorta with growth factor. (C), (D), (E) represent nifurtimox treatment at 1, 10 and 20 ug/ml concentrations in presence of growth factor.

TrkB is a receptor tyrosine kinase and is a high affinity receptor for neurotrophins. Activation of TrkB by neurotropins, similar to other Trks, has been implicated in differentiation as well as in suppressing apoptosis in neuronal cells[26]. TrkB is expressed almost exclusively in biologically unfavorable neuroblastomas[2,3]. BDNF binding to TrkB leads to the activation of the Ras/MAPK and PI3K/Akt signaling pathways. The Akt pathway has been shown to be critical for cell survival and resistance to chemotherapy[3,15]. As detailed in Example 3, when SMS-KCNR cells were stimulated with BDNF, phosphorylation of Akt due to activation of the TrkB receptor was inhibited in the presence of nifurtimox (FIG. 6A). This suggests that nifurtimox may act by inhibiting TrkB signaling. This finding is significant because the TrkB-BDNF pathway promotes cell survival and is known to protect cells from DNA damaging therapeutic agents in neuroblastoma cells leading to the development of chemoresistance[3,18,27]. Therefore drugs that inhibit this pathway are valuable in treating neuroblastoma. Additionally, nifurtimox decreased phosphorylation of Akt (FIG. 6B) suggesting that Akt may be a direct target of nifurtimox.

Similar to Akt, ERK1/2 phosphorylation is considered to promote survival and is activated by BDNF/TrkB pathway in neuroblastoma[26]. However, treatment of SMS-KCNR cells with nifurtimox did not alter the phosphorylation of ERK 1/2 phosphorylation (data not shown). These differential effects of nifurtimox likely reflect the unique functions of each pathway. For example, it has been reported that Akt mediates the promotion of cell survival induced by BDNF, where as, ERK1/2 mediates BDNF induced cell differentiation[28]. These studies indicate that nifurtimox can be a therapeutic agent to combat neuroblastoma.

Tested in vivo, Niurtimox treatment resulted in a significant decrease in tumor size in mice. See Example 12. In humans, Nifurtimox treatment, alone or in combination with other therapies, resulted in tumor regression without toxic side effects. Other researchers have found that Nifurtimox has many side effects in adults including nausea/vomiting, myalgia, weakness, headache, parasthesias, polyneuritis, psychotic disorders, and seizures[6] and have determined that it is much better tolerated in children, as seen in a study of 67 children using nifurtimox for Chagas disease[11]. However in our study described in detail in Examples 13 and 14, no patients have been excluded from the study due to adverse drug[5,11].

In conclusion, the examples show that Nifurtimox is cytotoxic to neuroblastoma cells. It inhibits proliferation and induces apoptosis in neuroblastoma. Apoptosis is mediated by the activation of caspase-3. Nifurtimox suppressed basal and TrkB mediated Akt phosphorylation suggesting inhibition of TrkB signaling. Thus, nifurtimox is a potent cytotoxic and apoptotic agent and can be a therapeutic agent to combat neuroblastoma.

EXAMPLES

Example 1

Reagent Preparation

Nifurtimox (from Bayer, Germany) was dissolved in dimethyl sulfoxide (DMSO) as a 20 mg/ml stock and stored in aliquots at −20° C. zVAD-fmk (Calbiochem La Jolla Calif.) was dissolved in DMSO at a concentration of 10 mM and stored at −20° C. Brain-derived neurotrophic factor (BDNF) was dissolved in sterile water (100 ng/ml) and stored at −80° C. (Santa Cruz Biotechnology, Santa Cruz, Calif.). Antibodies to cleaved caspase-3 and, phosphorylated and total forms of Akt, were obtained from Cell Signaling Technology, Beverly Mass., secondary anti-rabbit antibody coupled to HRP was from Amersham Pharmacia Biotech, Piscataway, N.J., and propidium Iodide was from Sigma Chemical Co., St Louis, Mo.

Example 2

Cell Culture and Treatment

The human neuroblastoma cell lines IMR-32 (ATCC), SMS-KCN, SMS-KCNR (from John Maris, CHOP, Philadelphia, Pa.) were maintained in RPMI 1640 media supplemented with 10% fetal bovine serum, 100 units/ml penicillin and 100 µg/ml streptomycin at 37° C. in a humidified incubator. Cells were grown in 6 well plates or 100 mm dishes to 75% confluency and serum deprived (RPMI 1640 with 0.1% BSA) overnight before treatment. Cells were treated with Nifurtimox (0, 1, 10, or 20 µg/ml) for 24 hours for caspase activation studies or for 2 hours and stimulated with 100 µg/ml BDNF (Santa Cruz Biotechnology, CA) for 10 minutes for analysis of Trk signaling.

Example 3

Nifurtimox Suppresses Akt Phosphorylation and TrkB Mediated Signaling

Figure 6B:
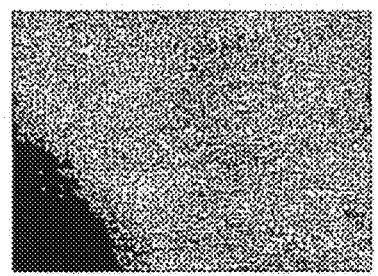
Figure 6C:
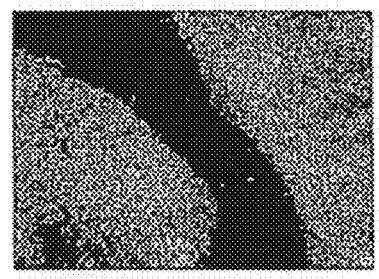
Figure 6D:
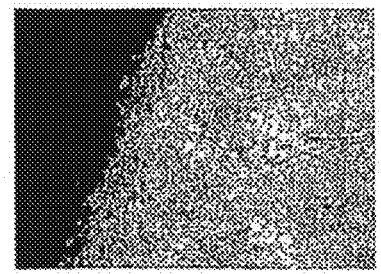
Figure 6E:
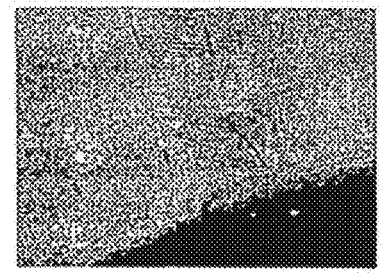

SMS-KCNR cells are known to express the TrkB receptor[14]. BDNF specifically stimulates the TrkB receptor on neuroblastoma cells and leads to phosphorylation of AktT[15] which plays a vital role in cell survival, ultimately leading to chemoresistance[3,15]. To understand the signaling pathways mediating the antiproliferative and cytotoxic effects of nifurtimox in neuroblastoma cells, TrkB and Akt signaling in SMS-KCNR cells was determined. Stimulation of SMS-KCNR cells with BDNF in the absence of nifurtimox resulted in an increased phosphorylation of Akt (FIG. 6A, Lane 1); however, addition of nifurtimox (10 and 20 µg/ml) significantly inhibited Akt phosphorylation as indicated by decreased band intensities (FIG. 6A, Lanes 3 and 4). Total Akt protein levels were not altered by nifurtimox (FIG. 6A). Furthermore, nifurtimox inhibited serum stimulated Akt phosphorylation (FIG. 6B). In the presence of serum, there were high levels of Akt activation (FIG. 6B, Lane 1); however, addition of nifurtimox abrogated the serum stimulated activation of Akt. At 1.0 and 10 µg/ml doses, nifurtimox completely inhibited the phosphorylation of. Akt (FIG. 6B, Lanes 2 and 3). These studies clearly showed that nifurtimox inhibits Akt signaling in neuroblastoma. On the other hand, phosphorylation of ERK1/2 (another downstream target of TrkB) was not affected. There was no change in the phosphorylation of ERK1/2 indicating that nifurtimox may not affect ERK mediated signaling (data not shown).

Example 4

Nifurtimox Suppresses the Cell Viability of Neuroblastoma Cells

The growth inhibitory effect of nifurtimox on SMS-KCN, SMS-KCNR and IMR-32 neuroblastoma cell lines was determined by MTS assay. Cell viability was measured using the CellTiter 96 AQ One Solution Cell Proliferation Assay kit (Promega, Madison Wis.)[4]. Cells were cultured (50,000 per well) in 48 well plates for 24 hours and treated with increasing concentrations of nifurtimox (0, 1, 10, and 20 μg/ml) for 24, 48, 72 and 96 hours. Vehicle treated cells were used as control (0.001% DMSO). At the end of the incubation period, MTS reagent (3-(4,5-dimethylthiazol-2-yl)-5-(3-carboxymethoxyphenyl)-2-(4-sulfophenyl)-2H-tetrazolium)[12] was added to each well in fresh media to a final concentration of 0.5 mg/ml and incubated for 4 hours. Absorbance was measured at 490 nm using a microplate reader (Multiskan RC, Fisher Scientific Pittsburgh, Pa.). Cell viability is represented as the mean percentage+/−SD of absorbance before and after treatment.

As shown in FIG. 2A, nifurtimox inhibited the growth of these cell lines significantly in a time and dose-dependent manner and was most pronounced in SMS-KCNR cells. The cell viability was decreased to 37% (SMS-KCNR), 59% (SMS-KCN), 78% (IMR-32) after 120 hours of treatment at 20 μg/ml nifurtimox. $IC_{50}$ values, the concentration required to reach 50% inhibition of growth, for these cell lines were determined to be 14.7 μg/ml for SMS-KCNR, 25.4 μg/ml for SMS-KCN and 52.9 μg/ml for IMR-32. These studies clearly show that nifurtimox is cytotoxic to neuroblastoma cell lines. Of importance is that such cytotoxic effects of nifurtimox are not observed with normal epithelial cells in culture Example 5

Nifurtimox Inhibits Neuroblastoma Cell Proliferation and DNA Synthesis

Cell viability is a sum total of events that include proliferation and cell death. First, we tested the ability of nifurtimox to inhibit DNA synthesis as a measure of its effect on proliferation. DNA synthesis was determined by measuring BrdU incorporation into DNA as a surrogate for proliferation.

Figure 2B:
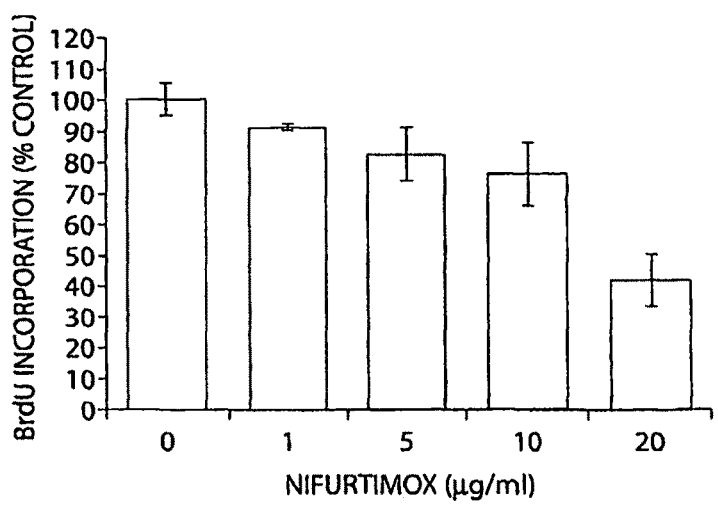
FIG. 2B is a histogram showing BrdU incorporation at different doses of nifurtimox. Cell proliferation assay: SMS-KCNR cells were cultured in 48 well plates and treated with 0, 1.0, 5.0, 10 and 20 μg/ml nifurtimox for 48 hours. DNA synthesis was determined by BrdU incorporation assay as described in the Example. Results are expressed as percentages of untreated controls and means of six replicates (±SD).
Figure 7:
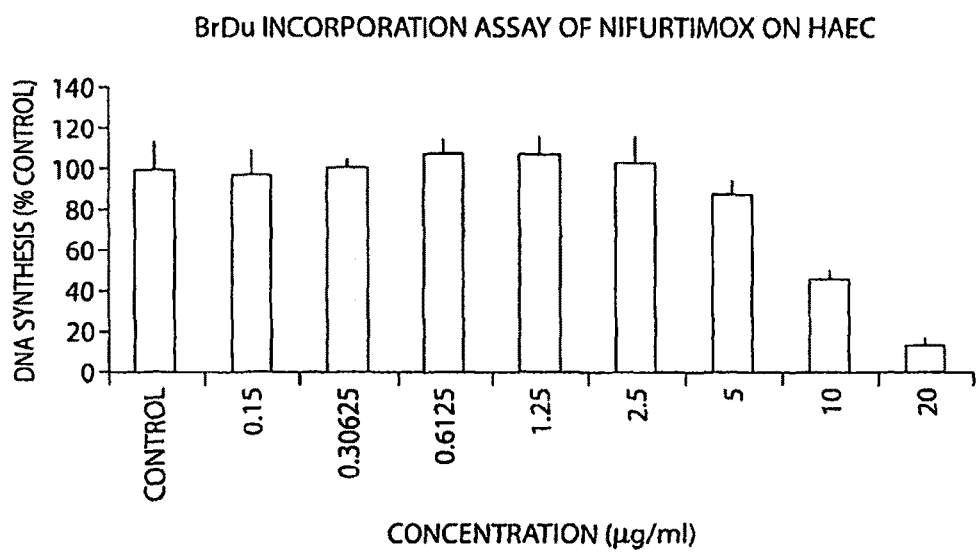
FIG. 7 is a histogram showing the inhibition of human aortic endothelial cell proliferation by nifurtimox in a dose dependent manner as reflected by the decreased incorporation of bromo deoxy uridine (BrDu) in the DNA synthesis.

The effect of nifurtimox on proliferation of neuroblastoma cell lines and endothelial cells was determined by BrdU (bromodeoxyuridine) incorporation assay during DNA synthesis[6,13] following manufacturer's instructions (Roche Molecular Biochemicals, Indianapolis Ind.). SMS-KCNR cells (50,000 per well) were cultured in 48 well plates for 24 hours, serum deprived for 18 hours and treated with nifurtimox (0, 1, 10, and 20 μg/ml) for 24 hours. Cells were labeled with 10 μM BrdU for 6 hours. The cells were fixed and the color was developed using peroxidase conjugated anti-BrdU antibody and TMB (3,3,5,5% tetramethylbenzidine) chromogenic substrate. Absorbance was measured at 450 nm using a microplate reader (Multiskan RC, Fisher Scientific, Pittsburgh, Pa.). In this assay, the color intensity correlates directly to the amount of BrdU incorporation which in turn reflects proliferation. The results are expressed as percentage of BrdU incorporation (+/−SD) and are shown in FIG. 2B. BrdU incorporation decreased with the increase in drug concentration indicating that nifurtimox inhibited DNA synthesis. A 50% inhibition in DNA synthesis was observed at 18.1 μg/ml nifurtimox. BrdU incorporation studies demonstrated that nifurtimox is a potent inhibitor of neuroblastoma cell proliferation. The results are shown in FIG. 7. When treated with nifurtimox, there was a dose dependent inhibition of DNA synthesis in HEC; a 50% inhibition was observed at 10 μg/ml nifurtimox, over 80% inhibition was observed at 20 μg/ml concentration nifurtimox and 30% inhibition was observed at concentrations as low as 5 μg/ml of nifurtimox. The BrdU incorporation studies demonstrate that nifurtimox is a potent inhibitor of HEC proliferation.

Example 6

Nifurtimox Induces Apoptosis of Neuroblastoma Cells

The cytotoxic effect of nifurtimox in neuroblastoma cells was further investigated to understand underlying mechanisms. SMS-KCNR cells were grown to 60% confluency in 48 well plates, incubated with increasing concentrations of nifurtimox for 96 hours. Vehicle treated cells were used as control. Following the treatment morphological features were initially observed with light microscopy using inverted microscope (Nikon Eclipse TS100, Japan) fitted with a Fuji digital camera (Japan). The cells were washed with PBS, fixed with paraformaldehyde, permeabilized with Triton X-100 at room temperature, labeled with fluorescein-12-dUTP using terminal deoxynucleotidyl transferase and counterstained with propidium iodide (5 μg/ml). Negative controls (without terminal transferase) were included in each experiment. Apoptosis was detected by fluorescence microscopy (Nikon Eclipse TE2000-E fitted with a cooled CCD camera, Japan). Propidium iodide staining was used to detect both non-apoptotic and apoptotic cells and fluorescein staining was used to detect the apoptotic cells.

Microscopic examination of nifurtimox treated cells revealed morphological alterations such as decreased axonal length, rounding and floating which are suggestive of apoptosis (FIG. 3A). The morphological changes were progressively pronounced with increased nifurtimox concentration. At 1 μg/ml nifurtimox, a decrease in axon length was apparent when compared to vehicle treated cells (FIG. 3 A-ii and A-I respectively). At 10 μg/ml nifurtimox, the decrease in axon length was more prominent and was associated with rounding of cells (FIG. 3A-*iii*). At 20 μg/ml nifurtimox, the cells were rounded up and floating with a few cells remained attached to the plate. (FIG. 3A-*iv*). Of importance is that these morphologic apoptotic changes occurred in a dose dependent manner.

Figure 3B:
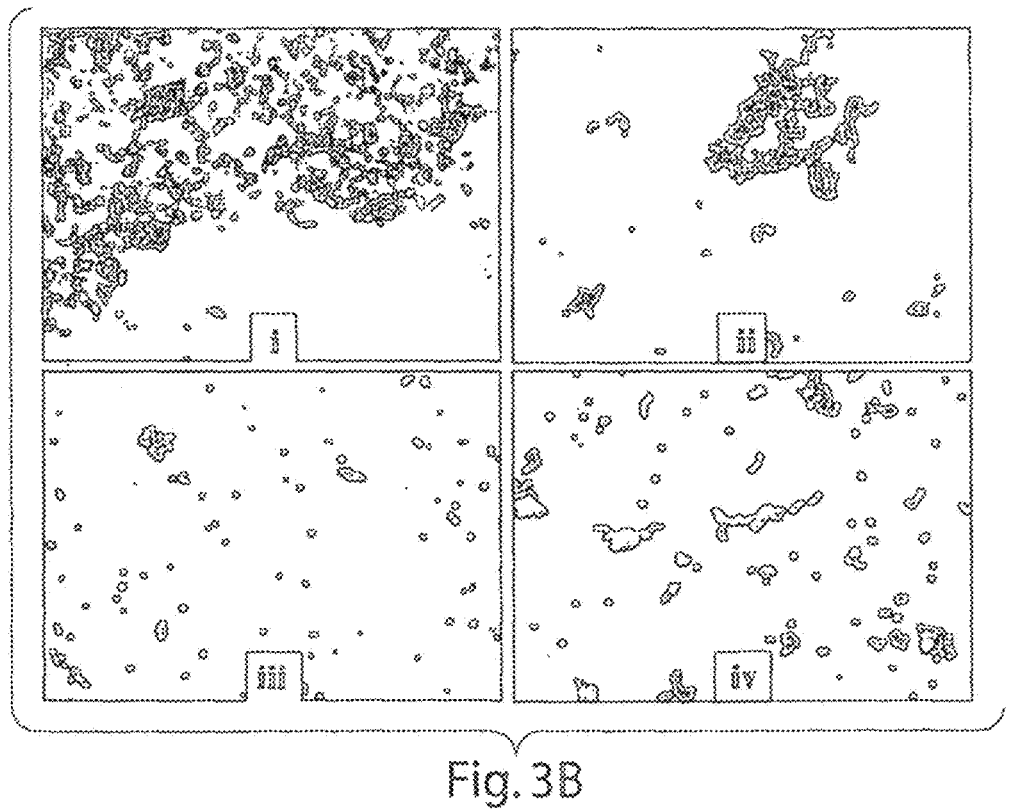
FIG. 3B is a set of pictures showing apoptotic cell death of neuroblastoma cells by nifurtimox. SMS-KCNR Cells were cultured and incubated with 0, 1.0, 10 and 20 μg/ml of nifurtimox for 96 hours, TUNEL assay was performed, photographed and processed as described in the Example. Magnification=100×. i to iv are representative pictures of overlaid apoptotic stain and nuclear stain. TUNEL positive nuclei due to DNA fragmentation in SMS-KCNR cells indicates occurrence of apoptotic cell death by nifurtimox treatment. (i): Vehicle control, (ii): 1 μg/ml, (iii): 10 μg/ml, and (iv): 20 μg/ml. The number of apoptotic nuclei increases with increasing nifurtimox dose.

TUNEL (terminal deoxynucleotidyltransferase-mediated deoxyuridine 5'-triphosphate (dUTP) nick-end labeling) assay was used to confirm the induction of apoptosis by nifurtimox. The terminal nucleotide transferase reaction was used to identify cell nuclei containing fragmented DNA in nifurtimox treated SMS-KCNR cells (0-20 μg/ml) for 96 hours. The nuclei were identified by red propidium iodide staining and TUNEL positive nuclei were identified by yellow spots in the PI and TUNEL overlay. The TUNEL assay shows a dose dependent increase in apoptosis in the SMS-KCNR cells after 72 hours of treatment with nifurtimox. With increasing drug concentration, increased apoptotic signal is seen in the nuclei of the cells (FIG. 3B).

Example 7

Western Blot Analysis

After treatment, the cells were collected by scraping and resuspended in 200 μl of E Buffer (10 mM Tris pH 7.6, 50 mM NaCl, 5 mM EDTA, 50 mM NaF, 0.1 mM NaVO4, 1% Triton, 10 ug/ml Aprotinin, 10 ug/ml Leupeptin, ABSF) and incubated on ice for 20 minutes to lyse the cells. Cell lysates were sonicated for 10 seconds and centrifuged for 20 minutes at 14,000 rpm at 4° C. Protein concentration was determined with BioRad protein estimation kit (BioRad, Hercules, Calif.). Cell lysates were electropheresed on a 12% SDS-PAGE and blotted onto PVDF (Polyvinylidene fluoride) membranes. The blots were blocked with 5% non-fat dry milk (BioRad, Hercules, Calif.) in PBST for 1 hour. The blots were probed with antibodies specific for cleaved caspase-3 and phosphorylated and total forms of Akt and ERK1/2. The protein bands were visualized using horseradish peroxidase-conjugated secondary antibodies (Amersham-Pharmacia Biotech, Piscataway, N.J.) followed by enhanced chemiluminescence (Upstate, Waltham, Mass.) and documented using BioRad, Gel Document System, GDS 8000 (BioRad, Hercules Calif.). Blots were stripped and probed with actin antibody as an internal loading control (Sigma Chemical Company, St. Louis, Mo.).

Example 8

BrdU Incorporation Assay of HEC

The effect of nifurtimox on proliferation was assessed by measuring BrdU incorporation during DNA synthesis. Human Endothelial Cells (HEC) (1×104 cells) were cultured in 96 well plates, serum deprived for 16 hours and treated with 0, 0.15, 0.3, 0.6125, 1.25, 2.5, 5 10 and 20 µg/ml in Medium 200 in the presence or absence of 50 ng/ml VEGF for 72 hours. BrdU (10 µM final concentration) was added to the cells and re-incubated for further 6 hours. The cells were fixed and the color was developed using anti-BrdU-POD antibody and TMB chromogenic substrate. The assay was performed according to the manufacturer's instructions. In this colorimetric cell proliferation assay, the color intensity correlates directly to the amount of BrdU incorporated into the DNA which in turn represents proliferation. The results are expressed as percentage BrdU incorporation.

Example 9

Role of Caspase-3 in Apoptosis by Nifurtimox; Caspase Inhibition Studies

Confirmation that nifurtimox treatment induces apoptosis was obtained by demonstrating activation of caspase-3, an initiator of the apoptotic cascade. SMS-KCNR cells were treated with 0, 1, 10 and 20 µg/ml nifurtimox for 24 hours and activation of caspase-3 was determined by immunoblot analysis using antibodies that recognize activated forms of caspase-3. The cell viability was measured by MTS assay as above. Minimal or basal level of caspase-3 activation was observed in vehicle treated cells (FIG. 4A). Addition of nifurtimox resulted in a dose dependent and strong activation of Caspase 3 as evidenced by the appearance of 19 and 17 kDa bands (FIG. 4A). Activation of caspase-3 by nifurtimox corroborated the increase in apoptosis shown by morphological observations and TUNEL assay (FIG. 3A, 3B).

To evaluate the critical role played by caspases in nifurtimox induced apoptosis in neuroblastoma cells, Z-VAD-FMK, a pancaspase inhibitor that irreversibly binds to the catalytic sites of caspases 1 through 9, was used. Inactivation of caspases results in inhibition of caspase mediated apoptosis. SMS-KCNR cells were pretreated with 50 µM pan-caspase inhibitor, Z-VAD-FMK for 90 minutes and then treated with nifurtimox (10 pg/ml) for 96 hours. SMS-KCNR cells were pretreated with 50 µM Z-VAD-FMK for 90 minutes before treatment with nifurtimox (10 µg/ml for 96 hours). This dose of 10 µg/ml nifurtimox was chosen because it is closer to $IC_{50}$ value (FIG. 2A). The cell viability was measured by MTS assay. Nifurtimox decreased the viability of SMS-KCNR cells by 50% compared to the vehicle treated control. However, addition of Z-VAD-FMK resulted in the reversal of the cytotoxic activity of nifurtimox (FIG. 4B). Pretreatment with 50 µM Z-VAD-FMK for 90 minutes increased cell viability to 90% in the presence of nifurtimox. These studies clearly showed that the cytotoxic effect of nifurtimox was reversed by pan-caspase inhibitor, Z-VAD-FMK suggesting that the observed apoptotic effect of nifurtimox was mediated by caspases.

Example 10

Nifurtimox Inhibits Angiogenesis—Tube Assay

First, we tested the effect of nifurtimox on tube formation on the Matrigel matrix. Stimulation with growth factors leads to morphological differentiation of endothelial cells and formation of tube like structures on matrices. The endothelial tube formation assay was performed in Matrigel bed. Briefly, Matrigel bed was prepared by using pre-cooled pipettes, plates and tubes on ice. Growth factor-reduced Matrigel was thawed overnight at 4° C. and mixed to homogeneity, Culture plates (48-well) were coated with 0.1 ml of Matrigel and allowed to gelatinize at 37° C. for 30 minutes. HEC ($2 \times 10^4$) per well were seeded on the Matrigel bed and cultured in EBM-2 basal media containing nifurtimox (0, 10 or 20 µg/ml) in the presence or absence of VEGF (50 ng/ml) for 8 hours. Capillary networks were photographed using a phase-contrast microscope (Nikon Eclipse TS100, fitted with Fuji digital camera, Japan), and the number of tubes was quantified by counting the branching points from four quadrants of each well.

Figure 8A:
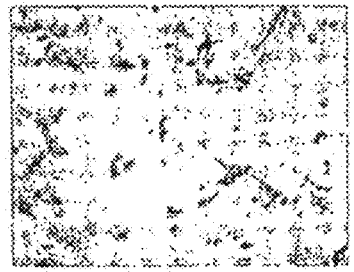
FIG. 8 (A-C) is a set of pictures showing the inhibition of tube formation, a critical step in the angiogenesis process by nifurtimox in a dose dependent manner. (A) Vehicle treated endothelial cells without growth factor (B) Vehicle treated endothelial cells with growth factor. (C) represents nifurtimox treatment at 20 ug/ml concentrations in presence of growth factor figure and quantitative graph. (D) is a histogram showing the quantitative analysis of the effect of nifurtimox on fuse formations assay.
Figure 8B:
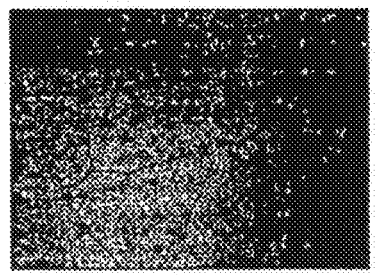
Figure 8C:
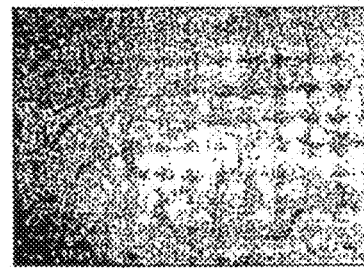
Figure 8D:
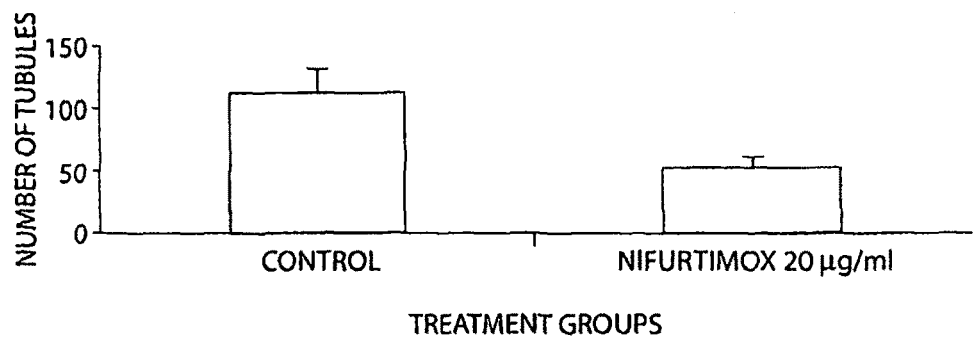
Figure 9:
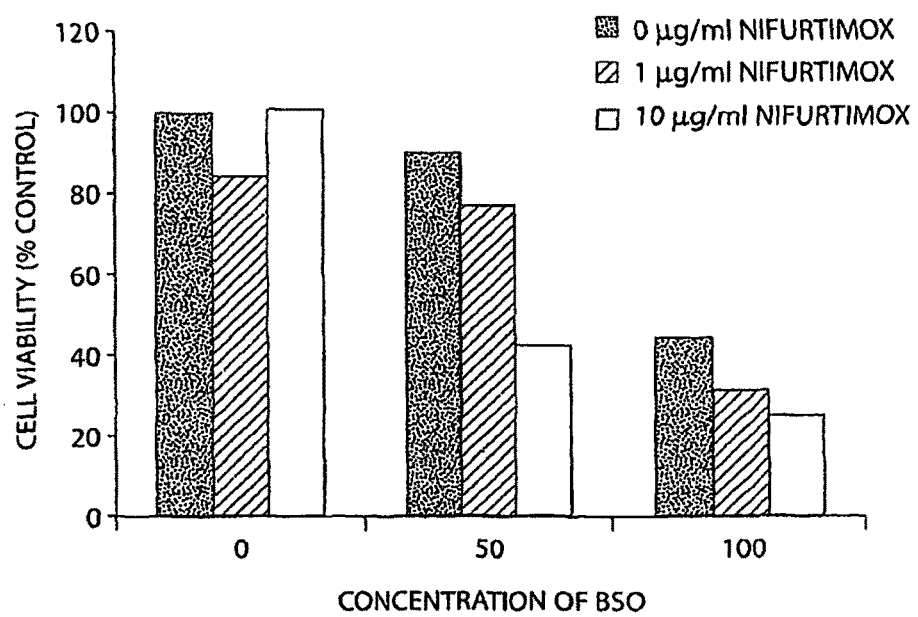
FIG. 9 is a histogram showing the effect of nifurtimox in combination with buthionine sulfoximine (BSO) on neuroblastoma cell viability. SMS KCNR cells were cultured overnight and then treated with 0, 1, or 10 μg/ml nifurtimox in combination with either 1, 50 or 100 μM BSO for 48 hours. Cell viability was measured with Calcein AM assay.
Figure 10:
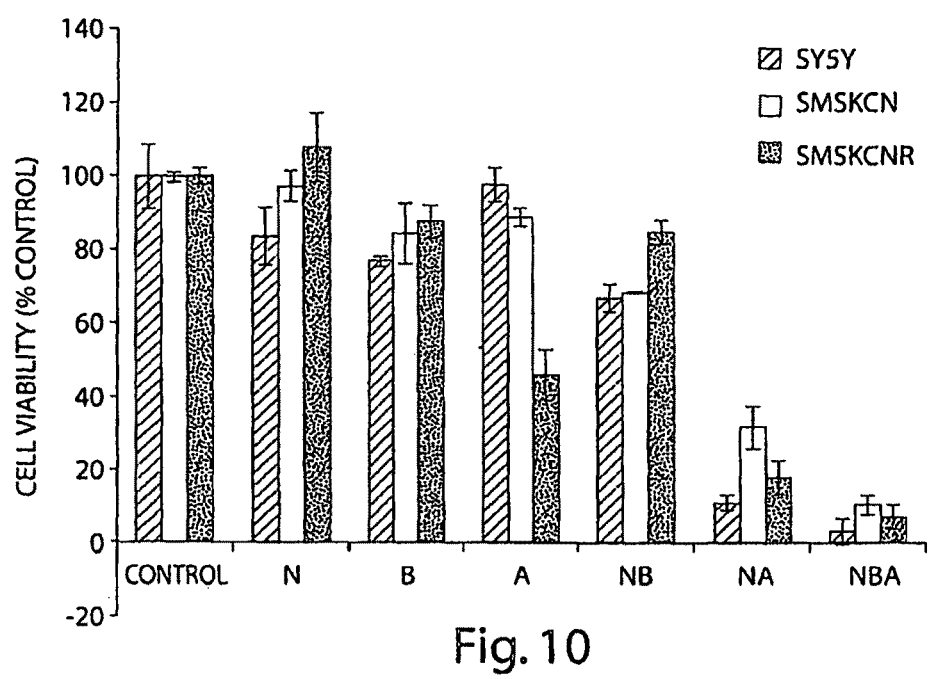
FIG. 10 is a histogram showing the effect of nifurtimox in combination with either ascorbic acid or BSO on neuroblastoma cell viability. SY5Y cells were cultured overnight and then treated with either 10 μg/ml nifurtimox (N), 0.3 mM ascorbic acid (A) or 50 μM BSO (B) alone or in combinations (NB, NA, NBA) for 24 hours. Cell viability was measured with Calcein AM assay. The results are expressed as a percent of vehicle control.

On Matrigel substratum, endothelial cells form aggregates, and then aggregated cells start to sprout and fuse to form tube-like structures. In the presence of growth factor HEC formed organized elongated tube-like structures resembling capillaries with an extensive network. (FIG. 8A). However, in the absence of growth factor (control), no such organized structures were observed (FIG. 8B). In the presence of VEGF, nifurtimox exhibited a marked inhibitory effect on the formation of tube-like structures by HEC. Tube formation was diminished with formation of incomplete network of capillary like structure (FIG. 8C). Nifurtimox showed 50% (±7%) inhibition of tube formation at 20 µg/ml respectively. These findings suggest that nifurtimox inhibits the tube formation step in angiogenesis.

Example 11

Nifurtimox Inhibits Angiogenesis—Aortic Ring Assay

Next, we tested the ability of nifurtimox to inhibit growth factor induced aortic capillary sprouts using rat aortic rings (explants) embedded in Matrigel beds. Matrigel bed mimics physiological extracellular matrix representing its natural composition and architecture. Due to these features, Matrigel enables several cell types, including endo-thelial cells, to maintain in culture their in vivo phenotype and 3-dimensional organization. Aortic arches were removed from euthanized rats and immediately transferred to a culture dish containing ice-cold serum-free media. The peri-aortic fibroadipose tissue was carefully removed with fine microdissection forceps and iridectomy scissors paying special attention not to damage the aortic wall. Aortic rings (1 mm thick) were sectioned and extensively rinsed in 5 consecutive washes of Medium 200. Ring shaped explants of rat aorta were then embedded in Matrigel beds in 48 well plates, treated with 1, 10 or 20 μg/ml nifurtimox in the presence or absence of growth factors and incubated at 37° C. in a tissue culture incubator. The explants were examined every second day with a Nikon Eclipse TS100 inverted microscope at an appropriate magnification and photographed at the end of 9th day. On the ninth day, the capillary sprouting were quantified by grading and recording the extent of sprouting directly reflecting angiogenesis using Nikon Eclipse TS100 fluorescent microscope (Japan) and Fuji digital camera.

The aortic rings cultured in serum free media showed little or no sprouting (FIG. 7A). When the aortic rings were cultured in the presence of growth factors (complete media), sprouting of microvessels were initially noticed in on day 3-4, with the number and length of microvessels increasing with prolonged culture time. Microvessel outgrowths arose from the edges of the implanted ring. The initially linear sprouts of HEC progressively branched, anatomized, and gave rise to a complex microvascular network. A thick capillary network of branching microvessels with tubes and loops developed from the periphery of the explant, which was found to spread towards the edges of the well (FIG. 7B). In contrast, this microvessel formation was dramatically decreased in a dose dependent manner when nifurtimox was added to complete media. A marked delay in outgrowth of the sprouts from the explants with a regression in both the number of microvessels and the number of branches was observed in nifurtimox treated aortic rings. At lower doses (1 and 10 μg/ml) of nifurtimox, the capillary network was sparse and incomplete (FIGS. 7C and D) and at higher doses of nifurtimox (20 μg/ml) there was complete inhibition of micro-vascular sprouting (FIG. 7E). The endothelial nature of the microvessels was demonstrated by staining the aortic rings with Dil-Ac-LDL (Data not shown). Dil-Ac-LDL is selectively taken up by endothelial cells and does not impair their growth, survival or functions. In accordance with their endothelial origin, the tubular outgrowths were fluorescent and corresponds to the phase contrast micrographs. Analysis of the out-growing microvessels revealed that nifurtimox strongly inhibited angiogenesis.

Example 12

Decrease in Tumor Size in Mice

Figure 11:
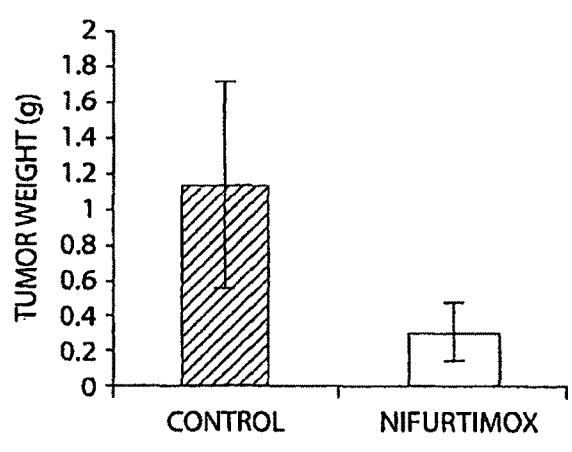
FIG. 11 is a histogram showing the effect of nifurtimox treatment on neuroblastoma xenograft mice as described in Example 12.

Xenograft experiments using $10^7$ SMS-KCNR cells injected into nude mice and treated with or without 150 mg/kg/day of nifurtimox in food pellets for 30 consecutive days. Upon harvest, tumor size was measured. The results are shown in FIG. 11. A greater than three fold decrease in tumor size was seen (1.14 grams versus 0.3 grams).

Example 13

Treatment of a Human Patient Having Neuroblastoma and Chagas Disease

A five year old female patient with progressive refractory neuroblastoma being treated with the conventional chemotherapeutics Cyclophosphamide (250 mg/m$^2$/dose in 50 ml/m$^2$ NS, infused over 30 minute) and Topotecan (0.75 mg/m$^2$/dose in 50 ml NS or D5W, infused over 30 minutes) acquired Chagas disease from a blood transfusion. Chagas disease is a parasitic disease caused by *Trypanasoma cruzi* endemic to South America. Although nifurtimox is not currently approved by FDA in the US for Chagas or any other diseases, it was obtained through the Center for Disease Control (CDC) in order to treat the Chagas disease in the patient.

The patient was started on a 15-20 mg/kg/day dose of Nifurtimox, by oral tablet three times daily; and the patient's tumor subsequently regressed'. When in remission and off all medications the patient relapsed, was restarted on nifurtimox, cyclyphosphamide and topotecan, and again demonstrated tumor regression. There were no significant side effects or evidence of significant organ toxicity in this patient.

Example 14

Treatment of Human Patients Having Neuroblastoma Only

Three additional patients with relapsed neuroblastoma (but not with Chagas disease) were treated with a 20 mg/kg/day (in three doses) of Nifurtimox alone or in combination with additional treatments as described below. All showed tumor regression and tolerated their treatment regimen well, with no significant side effects or evidence of organ toxicity.

|  | Age | Ascorbic Acid | Cyclophosphamide | Topotecan |
|---|---|---|---|---|
| Patient A | 4 | none | Beginning day 15, 250 mg/m$^2$/dose in 50 ml/m$^2$ NS, infused over 30 minute; daily for 5 consecutive days every 21 days, for 3 cycles | Beginning day 15, 0.75 mg/m$^2$/dose in 50 ml NS or D5W, infused over 30 minutes; daily for 5 consecutive days every 21 days, for 3 cycles |
| Patient B | 6 | 5 grams twice weekly, I.V. increased up to 25 grams twice weekly | 250 mg/m$^2$/dose in 50 ml/m$^2$ NS, infused over 30 minute; daily for 5 consecutive days every 21 days, for 3 cycles | 0.75 mg/m$^2$/dose in 50 ml NS or D5W, infused over 30 minutes; daily for 5 consecutive days every 21 days, for 3 cycles |
| Patient C | 9 | Beginning day 22, 5 grams twice weekly increased up to 30 grams twice weekly | 250 mg/m$^2$/dose in 50 ml/m$^2$ NS, infused over 30 minute; daily for 5 consecutive days every 21 days, for 3 cycles | 0.75 mg/m$^2$/dose in 50 ml NS or D5W, infused over 30 minutes; daily for 5, consecutive days every 21 days, for 3 cycles |

Patient A presented with multiply relapsed neuroblastoma and was started on Nifurtimox at the dosage described above. After two weeks the patient's quality of life had improved and tumor stabilization was observed. After four months of treatment with Nifurtimox co-administered with cyclophosphamide and topotecan, significant and continuous tumor regression was observed. After two months on the treatment regimen, Patient B had normalization of tumor markers; bone marrow aspirate was clear and negative for disease and MIBG scan, which had multiple spots upon presentation, showed one spot remaining. Patient C had an initial tumor marker VMA of 22 and bone marrow positive for tumor. By Day 21 prior to the start of ascorbic acid co-administration, the patient's tumor marker VMA bad decreased to 17 and the patient's bone marrow was negative. After 3 cycles of treatment, the patient's tumor marker VMA had further decreased to 13.

Example 15

Dose Toxicity Studies in Human Patients

The standard therapeutic dose in children for the treatment of Chagas disease is 15-20 mg/kg/day. Toxicity at these doses is generally mild. For dose toxicity studies, escalating dosages as set forth in the following table are used.

| Dose Escalation | | |
|---|---|---|
| Level | Number of Patients/group | Dose (mg/kg/day) |
| 1 | 3 | 20 |
| 2 | 3 | 30 |
| 3 | 3 | 40 |
| 4 | 3 | 50 |
| 5 | 3 | 60 |

On days 1-21, the patients are treated with Nifurtimox alone in oral dosages three times per day. Thereafter, Cyclophosphamide and topotecan are added to the Nifurtimox treatment regimen Each cycle of chemotherapy is given over 5 consecutive days every 21 days as follows: Prehydration with 500 ml/m$^2$ D5W ½ NS over 30-60 minutes, along with antiemetic therapy. Cyclophosphamide, 250 mg/m$^2$/dose in 50 ml/m$^2$ NS, infused over 30 minute. Topotecan, 0.75 mg/m$^2$/dose in 50 ml NS or D5W, infused over 30 minutes. FILGRASTIM, 5 micrograms/kg sc daily is given beginning 24-48 hours after the completion of day 5 chemotherapy and until neutrophil recovery. PEG-filgrastim 6 mg sc may be substituted for patients >40 kg at the discretion of the treating physician.

This 21 day cycle is repeated for a total of 3 times with re-evaluation prior to each cycle. Re-evaluation will include CBC, LDH, ferritin, urine catecholamines, MRI of primary site, and MIBG scan, plus bone marrow aspiration/biopsy if positive at beginning of protocol. Treatment beyond the 4 cycles of therapy is left up to the discretion of the treating physician.

Example 16

Improved Synthesis of Nitrofurans (Specifically Nifurtimox)

Figure 12:
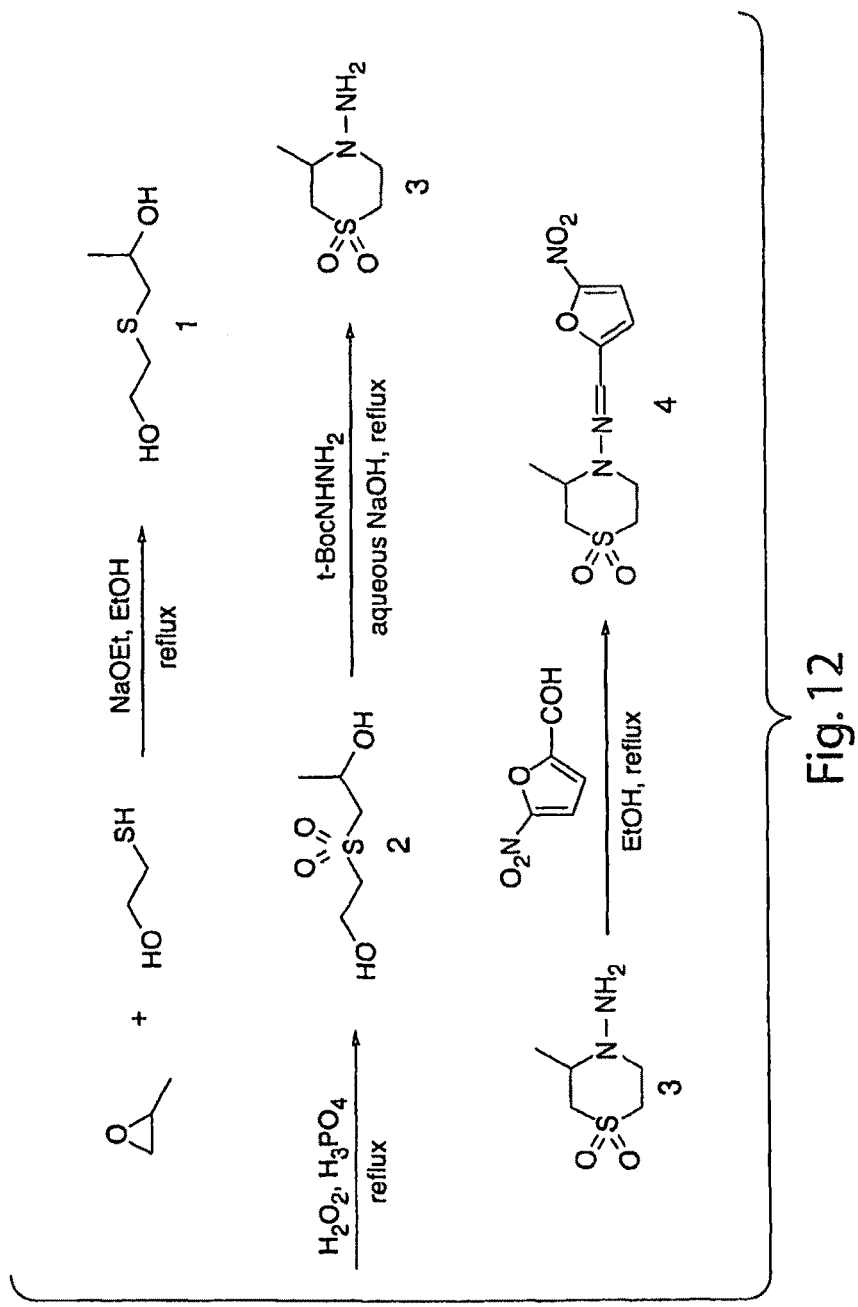
FIG. 12 is a schematic diagram illustrating the scheme for the synthesis of the nitrofuran compounds of the invention as described in detail in Example 16.

An improved, more efficient, and less hazardous synthesis of the nitrofuran side chain was accomplished and is illustrated in FIG. 12 and described below.

Referring to FIG. 12, the synthesis of diol (1) was achieved with base promoted nucleophilic addition of mercaptoethanol to propylene oxide at reflux in ethanol as solvent. As known by those skilled in the art, this reaction is achievable with solvents other than ethanol and with bases other than sodium ethoxide.

$^1$H NMR (CDCl$_3$): δ 3.868 (1H), 3.734 (2H), 2.725 (4H), 2.465 (2H), 1.222 (3H) MS (FAB): 159 [H+Na]$^+$

The synthesis of sulfone diol (2) was achieved with hydrogen peroxide solution under catalytic amounts of acids, such as phosphoric acid, at reflux. The solvent was removed under reduced pressure or under stream of air, N$_2$ or argon and then dried under high vacuum.

$^1$H NMR (CDCl$_3$): δ 4.48 (1H), 4.12 (2H), 3.31 (3H), 3.13 (1H), 1.31 (3H); MS (FAB):191 [M+Na]$^+$.

The cyclization of sulfone diol (2) (1 eq.) to compound (3) was achieved by base promoted hydrazine insertion with tBoc-NHNH$_2$ (1.25 eq) at reflux overnight. The reaction mixture was extracted with ethyl acetate and concentrated under reduced pressure to afford a semi solid product.

MS (FAB): 165.2 [M+H]$^+$, 187 [M+Na]$^+$.

The synthesis of Nifurtimox was achieved by condensation of compound (3) (1.1 eq.) with 5-nitro-2-furaldehyde (1 eq.) at reflux, for periods of up to 24 hrs, in alcoholic solvents such as ethyl alcohol, preferably anhydrous. The reaction mixture was filtered hot or cold under suction and afforded the desired product.

$^1$H NMR (CDCl$_3$+CD$_3$OD): δ 7.40 (1H), 7.32 (1H), 6.67 (1H), 4.16-4.23 (1H), 3.98-4.04 (1H), 3.64-3.74 (1H), 2.80-3.02 (4H) and 1.45-1.47 (d, 3H)

All of the compositions and methods disclosed and claimed herein can be made and executed without undue experimentation in light of the disclosure. Although the compositions and methods of the invention have been described in terms of preferred embodiments, it will be apparent to those having ordinary skill in the art that variation may be made to the compositions and methods without departing from the concept, spirit and scope of the invention. For example, certain agents and composition that are chemically related may be substituted for the agents described herein if the same or similar results would be achieved. All such similar substitutes and modifications apparent to those skilled in the art are deemed to be within the spirit, scope and concept of the invention.

All publications, patent applications, patents and other documents cited herein are incorporated by reference in their entirety. In case of conflict, this specification including definitions will control. In addition the material, methods and examples are illustrative only and not intended to be limiting.

REFERENCES

1. Brodeur G M, Pritchard J, Berthold F, et al., Revisions of the international criteria for neuroblastoma diagnosis, staging, and response to treatment. J Clin Oncol 1993; 11:1466-1477.
2. Brodeur G M, Maris J M, Yamashiro D J, Hogarty M D, White P S. Biology and Genetics of Human Neuroblastomas. J Pediatr Hematol Oncol 1997; 19:93-101.
3. Ho R, Eggert A, Hishiki T. et al., Resistance to Chemotherapy Mediated by TrkB in Neuroblastomas. Cancer Res 2002; 62:6462-6466.
4. Raether W, Hanel H. Nitroheterocyclic Drugs with Broad Spectrum Acitivity, Parasit Res 2003; 90:S19-S39.
5. Hiraki Y, Sekine A, Nabeshi H, Midorikawa K, Murata M, Kumagai Y, Kawanishi S. Mechanism of carcinogenesis induced by a veterinary antimicrobial drug, nitrofurazone, via oxidative DNA damage and cell proliferation. Cancer Letters 2004; 215:141-150.
6. Castro J, Diaz De Toranzo E G. Toxic Effects of Nifurtimox and Benznidazole, Two Drugs used against American Trypanosomiasis (Chagas' Disease). Biomed Environ Sci 1988; 1:19-33.
7. Faundez M, Pino L, Letelier P. et al., Buthionine sulfoximine increases the toxicity of nifurtimox and benznidazole to *Trypanosoma cruzi*. Antimicrob Agents Chemother 2005; 49:126-30.
8. Docampo R, Stoppani A O M. Generation of Superoxide anion and Hydrogen Peroxide induced by Nifurtimox in *Trypanosoma cruzi*. Arch Biochem Biophys 1979; 197: 317-321.
9. Montalto do Mecca M, Diaz E G, Castro J A. Nifurtimox biotransformation to reactive metabolites or nitrite in liver subcellular fractions and model systems. Toxicol Lett 2002; 136:1-8.
10. Muelas-Serrano S, Perez-Serrano J, Gomez-Barrio A, Aran V J, Rodriguez-Caabeiro. F. Untrastructural Alterations Induced by Nifurtimox and another Nitro Derivative on Epimastigotes of *Trypanasoma cruzi*. Parasitol Res 2002; 88:97-101.
11. Solari A, Ortiz S, Soto A, et al., Treatment of *Trypanosoma cruzi*-infected children with Nifurtimox: a 3 year follow-up by PCR. J Antimicrob Chemother 2001; 48:515-519.
12. Malich G, Markovic B, Winder C, The sensitivity and specificity of the MTS tetrazolium assay for detecting the in vitro cytotoxicity of 20 chemicals using human cell lines. Toxicology 1997; 124:179-192.
13. Gratzner H G. Monoclonal antibody to 5-bromo- and 5-iodo-deoxyuridine: A new reagent for detection of DNA replication. Science 1982; 218:474-475.
14. Feng X, Jiang H, Baik J C, Edgar C, Eide F F. BDNF Dependence in Neuroblastoma. J Neurosci Res 2001; 64(4):355-63.
15. Jaboin J, Kim C J, Kaplan D R, Thiele C J. Brain-derived Neurotrophic Factor Activation of TrkB Protects Neuroblastoma Cells from Chemotherapy-induced Apoptosis via Phosphatidylinositol 3'-Kinase Pathway. Cancer Res 2002; 62:6756-6763.
16. Reynolds C P, Biedler J L, Spengler B A, Reynolds D A, Eoss R A, Frenkel E P, Smith R G, Characterization of human neuroblastoma cell lines established before and after therapy. J Natl Cancer Inst 1986; 76:375-87.
17. Moreno S N J, Mason R P, Docampo R. Reduction of Nifurtimox and Nitrofurantoin to Free Radical Metabolites by Rat Liver Mitochondria. J Biol Chem 1984; 259:6298-6305.
18. Hileman E O, Liu J, Albitar M, Keating M J, Huang P. Intrinsic Oxidative Stress in Cancer Cells: a Biochemical Basis for Therapeutic Selectivity. Cancer Chemother Pharmacol 2004; 53:209-219.
19. Behrend L, Henderson G, Zwacka R M. Reactive Oxygen Species in Oncogenic Transformation. Biochem Soc Trans 2003; 31:1441-1444.
20. Carreras M C, Franco M C, Peralta J G, Poderoso J J. Nitric Oxide, complex I, and the Modulation of Mitochondrial Reactive Oxygen Species in Biology and Disease. Mol Aspects Med 2004; 25:125-139.
21. Muelas-Serrano S, Le-Senne A, Fernandez-Portillo C, Nogal JJ, Ochoa S, Gomez-Barrio A. In Vitro and In Vivo Anti-*Trypanosoma cruzi* Activity of a Novel Nitro-derivative. Mem Inst Oswaldo Cruz 2002; 97:553-557.
22. Attanasio A, Schiffer D. Ultrastructural Delection of DNA Strand Breaks by in situ End-labeling Techniques. J Pathol 1995; 176:27-35.
23. Thornberry NA, Lazebnik Y. Caspases: enemies within. Science 1998; 281: 1312-1316.
24. Van Noorden CJ. The History of Z-VAD-FMK, a Tool for Understanding the Significance of Caspase Inhibition. Acta Histochem 2001; 103:241-251.
25. Puppo M, Pastorino S, Melillo G, Pezzolo A, Varesio L, Bosco MC. Induction of Apoptosis by Flavopiridol in Human Neuroblastoma Cells is Enhanced under Hypoxia and Associated with N-myc Proto-Oncogene Down Regulation. Clin Cancer Res 2004; 10:8704-8719.
26. Hetman M, Xia Z. Signaling pathways mediating anti-apoptotic action of neurotrophins. Acta Neurobiol Exp 2000; 60:531-545.
27. Middlemas D S, Kihl B K, Zhou J, Zhu X. Brain-derived Neurotrophic Factor promotes Survival and Chemoprotection of Human Neuroblastoma Cells. J Biol Chem 1999; 274:16451-16460.
28. Encinas M, Iglesias M, Llecha N, Comella D C. Extracellular-regulated kinases and phosphatidylinositol 3-kinase are involved in brain-derived neurotrophic factor-mediated survival and neuritogenesis of the neuroblastoma cell line SH-SY5Y. J Neurochem 1999:73:1409-21.

We claim:
1. A method for treating a cancer or inhibiting angiogenesis in a mammal, comprising the step of: administering to a mammal having the cancer a therapeutically effective amount of Nifurtimox.
2. The method according to claim 1, wherein the cancer is neuroblastoma, medulloblastoma, peripheral malignant nerve sheath tumor, ependymoma, chraniopharyngioma, astrocytoma, meningioma, germinoma, glioma, mixed glioma, choroid plexus tumor, oligodendroglioma, peripheral neuroectodennal tumor, primitive neuroectodermal tumor (PNET), CNS lymphoma, pituitary adenoma, Schwannoma, basal cell carcinoma, biliary tract cancer, bladder cancer, bone cancer, breast cancer, cervical cancer, choriocarcinoma, colon and rectum cancer, connective tissue cancer, endometrial cancer, esophageal cancer, eye cancer, fibroma, gastric cancer, intra-epithelial neoplasm, kidney cancer, larynx cancer, acute myeloid leukemia, acute lymphoid leukemia, chronic myeloid leukemia, chronic lymphoid leukemia, liver cancer, small cell lung cancer, non-small cell lung cancer, Hodgkin's and Non-Hodgkin's lymphoma, melanoma, oral cavity cancer, ovarian cancer, pancreatic cancer, prostate cancer, retinoblastoma, rhabdomyosarcoma, rectal cancer, renal cancer, skin cancer, stomach cancer, testicular cancer, thyroid cancer, uterine cancer, or cancer of the urinary system cancer of the urinary system.
3. The method according to claim 2, wherein the cancer is neuroblastoma.
4. The method according to claim 1, wherein the Nifurtimox is in a form suitable for administration orally, intrathecally, intracranially or intramuscularly.
5. The method according to claim 1, wherein the Nifurtimox is present in a medicament in an amount to give a unit dosage of 200-300 mg.
6. The method according to claim 5 wherein the Nifurtimox is to be administered at intervals ranging from once a day to once three times a day.
7. The method according to claim 6 wherein the Nifurtimox is to be administered three times per day for three weeks.

8. The method according to claim 1, wherein the Nifurtimox further comprises a thereapeutically effective and physiologically acceptable amount of at least one other active ingredient or agent.

9. The method according to claim 8, wherein the at least one other active ingredient is ascorbic acid or buthionine sulfoximine.

10. The method of claim 1, wherein the therapeutically effective amount of Nifurtimox is 0.1 µg/Kg/day to 200 mg/Kg/day for the mammal.

11. The method of claim 1, wherein the therapeutically effective amount of Nifurtimox is 0.5 mg/Kg/day to 150 mg/Kg/day for the mammal.

12. The method of claim 1, wherein the therapeutically effective amount of Nifurtimox is 1 mg/Kg/day to 100 mg/Kg/day for the mammal.

* * * * *

UNITED STATES PATENT AND TRADEMARK OFFICE
CERTIFICATE OF CORRECTION

| | | |
|---|---|---|
| PATENT NO. | : 8,470,815 B2 | Page 1 of 1 |
| APPLICATION NO. | : 12/225202 | |
| DATED | : June 25, 2013 | |
| INVENTOR(S) | : Saulnier Sholler et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 672 days.

Signed and Sealed this
Sixteenth Day of December, 2014

Michelle K. Lee
*Deputy Director of the United States Patent and Trademark Office*